(12) United States Patent
Arbefeuille et al.

(10) Patent No.: US 10,390,930 B2
(45) Date of Patent: Aug. 27, 2019

(54) METHOD FOR AORTIC BRANCHED VESSEL REPAIR

(71) Applicant: Bolton Medical, Inc., Sunrise, FL (US)

(72) Inventors: Samuel Arbefeuille, Sunrise, FL (US); Fletcher Christian, Sunrise, FL (US); Joseph A. Manguno, Jr., Sunrise, FL (US); John C. Canning, Sunrise, FL (US)

(73) Assignee: Bolton Medical, Inc., Sunrise, FL (US)

( * ) Notice: Subject to any disclaimer, the term of this patent is extended or adjusted under 35 U.S.C. 154(b) by 187 days.

(21) Appl. No.: 15/417,467

(22) Filed: Jan. 27, 2017

(65) Prior Publication Data

US 2017/0135807 A1 May 18, 2017

Related U.S. Application Data

(60) Division of application No. 13/788,724, filed on Mar. 7, 2013, now Pat. No. 9,592,112, which is a
(Continued)

(51) Int. Cl.
*A61F 2/07* (2013.01)
*A61F 2/966* (2013.01)
(Continued)

(52) U.S. Cl.
CPC ............... *A61F 2/07* (2013.01); *A61F 2/966* (2013.01); *A61F 2/89* (2013.01); *A61F 2/954* (2013.01);
(Continued)

(58) Field of Classification Search
CPC .. A61F 2/95; A61F 2/954; A61F 2/966; A61F 2002/9505; A61F 2002/9511;
(Continued)

(56) References Cited

U.S. PATENT DOCUMENTS 4,501,263 A 2/1985 Harbuck
5,231,989 A 8/1993 Middleman et al.
(Continued)

FOREIGN PATENT DOCUMENTS

EP 1 487 380 B1 2/2008
EP 2 051 663 B1 11/2009
(Continued)

OTHER PUBLICATIONS

"Bolton Medical Thoracic Branch Graft Case Presentation," Charing Cross Symposium Annual Meeting, London, Apr. 8-12, 2011.
(Continued)

*Primary Examiner* — Katherine M Rodjom
(74) *Attorney, Agent, or Firm* — Saul Ewing Arnstein & Lehr LLP; Mary K. Murray; N. Scott Pierce

(57) ABSTRACT

An aortic graft assembly includes a tubular component that defines a wall aperture having a proximal end that extends perpendicular to a major longitudinal axis of the tubular aortic component, and a tunnel graft connected to the wall of the tubular aortic component and extending from the wall aperture toward a proximal end of the tubular aortic component. The method for delivery of the aortic graft assembly includes delivering the aortic graft assembly through the wall aperture and into interfering relation with the tunnel graft.

17 Claims, 35 Drawing Sheets

Related U.S. Application Data continuation of application No. PCT/US2012/065622, filed on Nov. 16, 2012.

(60) Provisional application No. 61/560,517, filed on Nov. 16, 2011.

(51) Int. Cl.

| | | |
|---|---|---|
| A61F 2/954 | (2013.01) | |
| A61F 2/95 | (2013.01) | |
| A61F 2/06 | (2013.01) | |
| A61F 2/89 | (2013.01) | |
| A61F 2/82 | (2013.01) | |

(52) U.S. Cl.
CPC ... *A61F 2002/061* (2013.01); *A61F 2002/067* (2013.01); *A61F 2002/075* (2013.01); *A61F 2002/821* (2013.01); *A61F 2002/9505* (2013.01); *A61F 2002/9665* (2013.01); *A61F 2220/0075* (2013.01); *A61F 2250/0098* (2013.01)

(58) Field of Classification Search
CPC ...... A61F 2002/9517; A61F 2002/9534; A61F 2002/9665; A61F 2/07; A61F 2002/061; A61F 2002/067

See application file for complete search history.

(56) References Cited

U.S. PATENT DOCUMENTS

| | | | |
|---|---|---|---|
| 5,575,817 | A | 11/1996 | Martin |
| 5,683,449 | A | 11/1997 | Marcade |
| 5,755,772 | A | 5/1998 | Evans et al. |
| 5,855,598 | A | 1/1999 | Pinchuk |
| 5,984,955 | A | 11/1999 | Wisselink |
| 6,059,824 | A | 5/2000 | Taheri |
| 6,187,033 | B1 | 2/2001 | Schmitt et al. |
| 6,210,429 | B1 | 4/2001 | Vardi et al. |
| 6,306,141 | B1 | 10/2001 | Jervis |
| 6,344,056 | B1 | 2/2002 | Dehdashtian |
| 6,395,018 | B1 | 5/2002 | Castaneda |
| 6,428,565 | B1 | 8/2002 | Wisselink |
| 6,585,756 | B1 | 7/2003 | Strecker |
| 6,592,615 | B1 | 7/2003 | Marcade et al. |
| 6,595,963 | B1 | 7/2003 | Barbut |
| 6,645,242 | B1 | 11/2003 | Quinn |
| 6,676,699 | B2 | 1/2004 | Shiu |
| 6,814,752 | B1 | 11/2004 | Chuter |
| 7,144,421 | B2 | 12/2006 | Carpenter et al. |
| 7,294,147 | B2 | 11/2007 | Hartley |
| 7,407,509 | B2 | 8/2008 | Greenberg et al. |
| 7,438,721 | B2 | 10/2008 | Doig et al. |
| 7,537,606 | B2 | 5/2009 | Hartley et al. |
| 7,550,004 | B2 | 6/2009 | Bahler et al. |
| 7,641,646 | B2 | 1/2010 | Kennedy, II |
| 7,731,744 | B1 | 6/2010 | Cox |
| 7,763,063 | B2 | 7/2010 | Arbefeuille et al. |
| 7,828,837 | B2 | 11/2010 | Khoury |
| 7,854,758 | B2 | 12/2010 | Taheri |
| 7,914,572 | B2 | 3/2011 | Hartley et al. |
| 8,007,605 | B2 | 8/2011 | Arbefeuille et al. |
| 8,021,419 | B2 | 9/2011 | Hartley et al. |
| 8,048,140 | B2 | 11/2011 | Purdy |
| 8,052,736 | B2 | 11/2011 | Doig et al. |
| 8,062,345 | B2 | 11/2011 | Ouellette et al. |
| 8,062,349 | B2 | 11/2011 | Moore et al. |
| 8,070,790 | B2 | 12/2011 | Berra et al. |
| 8,092,511 | B2 | 1/2012 | Chuter |
| 8,105,372 | B1 | 1/2012 | Chuter |
| 8,167,930 | B2 | 5/2012 | Allen et al. |
| 8,172,895 | B2 | 5/2012 | Anderson et al. |
| 8,267,988 | B2 | 9/2012 | Hamer et al. |
| 8,273,115 | B2 | 9/2012 | Hamer et al. |
| 8,292,943 | B2 | 10/2012 | Berra et al. |
| 8,308,790 | B2 | 11/2012 | Arbefeuille et al. |
| 8,333,800 | B2 | 12/2012 | Bruszewski et al. |
| 8,337,546 | B2 | 12/2012 | Bruszewski |
| 8,361,134 | B2 | 1/2013 | Hartley et al. |
| 8,394,136 | B2 | 3/2013 | Hartley et al. |
| 8,449,595 | B2 | 5/2013 | Ouellette et al. |
| 8,474,120 | B2 | 7/2013 | Hagaman et al. |
| 8,500,792 | B2 | 8/2013 | Berra |
| 8,523,934 | B2 | 9/2013 | Purdy |
| 8,545,549 | B2 | 10/2013 | Hartley et al. |
| 8,556,961 | B2 | 10/2013 | Quinn |
| 8,574,284 | B2 | 11/2013 | Roeder et al. |
| 8,574,288 | B2 | 11/2013 | Hartley et al. |
| 8,636,788 | B2 | 1/2014 | Arbefeuille et al. |
| 8,663,310 | B2 | 3/2014 | Greenberg et al. |
| 8,672,993 | B2 | 3/2014 | Chuter et al. |
| 8,728,145 | B2 | 5/2014 | Chuter et al. |
| 8,740,963 | B2 | 6/2014 | Arbefeuille et al. |
| 8,740,966 | B2 | 6/2014 | Brocker et al. |
| 8,753,386 | B2 | 6/2014 | Shaw |
| 8,795,349 | B2 | 8/2014 | Huser et al. |
| 8,808,358 | B2 | 8/2014 | Khoury |
| 8,870,939 | B2 | 10/2014 | Roeder et al. |
| 8,870,946 | B1 | 10/2014 | Quinn |
| 8,940,040 | B2 | 1/2015 | Shahriari |
| 8,945,202 | B2 | 2/2015 | Mayberry et al. |
| 8,945,205 | B2 | 2/2015 | Greenberg |
| 8,992,593 | B2 | 3/2015 | Chuter et al. |
| 8,998,970 | B2 | 4/2015 | Arbefeuille et al. |
| 9,034,027 | B2 | 5/2015 | Ivancev |
| 9,095,456 | B2 | 8/2015 | Ivancev et al. |
| 9,101,455 | B2 | 8/2015 | Roeder et al. |
| 9,101,506 | B2 | 8/2015 | Arbefeuille et al. |
| 9,149,382 | B2 | 10/2015 | Greenberg et al. |
| 9,173,755 | B2 | 11/2015 | Berra et al. |
| 9,198,786 | B2 | 12/2015 | Moore et al. |
| 9,220,617 | B2 | 12/2015 | Berra et al. |
| 9,259,336 | B2 | 2/2016 | Schaeffer et al. |
| 9,320,631 | B2 | 4/2016 | Moore et al. |
| 9,333,104 | B2 | 5/2016 | Ouellette et al. |
| 9,345,595 | B2 | 5/2016 | Brocker et al. |
| 9,364,314 | B2 | 6/2016 | Berra et al. |
| 9,408,734 | B2 | 8/2016 | Arbefeuille et al. |
| 9,408,735 | B2 | 8/2016 | Arbefeuille et al. |
| 9,439,751 | B2 | 9/2016 | White et al. |
| 9,554,929 | B2 | 1/2017 | Arbefeuille et al. |
| 9,561,124 | B2 | 2/2017 | Arbefeuille et al. |
| 9,592,112 | B2 | 3/2017 | Arbefeuille et al. |
| 9,597,209 | B2 | 3/2017 | Khoury |
| 9,649,188 | B2 | 5/2017 | Hartley |
| 9,655,712 | B2 | 5/2017 | Berra et al. |
| 9,724,187 | B2 | 8/2017 | Ivancev et al. |
| 9,855,130 | B2 | 1/2018 | Roeder et al. |
| 9,861,505 | B2 | 1/2018 | Khoury |
| 9,877,857 | B2 | 1/2018 | Arbefeuille et al. |
| 9,907,686 | B2 | 3/2018 | Ouellette et al. |
| 9,913,743 | B2 | 3/2018 | Arbefeuille et al. |
| 9,925,080 | B2 | 3/2018 | Arbefeuille et al. |
| 10,105,248 | B2 | 10/2018 | Berra et al. |
| 10,105,250 | B2 | 10/2018 | Berra |
| 10,182,930 | B2 | 1/2019 | Moore et al. |
| 10,213,291 | B2 | 2/2019 | Berra et al. |
| 2002/0052643 | A1 | 5/2002 | Wholey et al. |
| 2003/0120333 | A1 | 6/2003 | Ouriel et al. |
| 2003/0199967 | A1 | 10/2003 | Hartley et al. |
| 2003/0204242 | A1 | 10/2003 | Zarins et al. |
| 2004/0006299 | A1 | 1/2004 | Barbut |
| 2004/0215327 | A1 | 10/2004 | Doig et al. |
| 2005/0010277 | A1 | 1/2005 | Chuter |
| 2005/0059923 | A1 | 3/2005 | Gamboa |
| 2005/0102018 | A1 | 5/2005 | Carpenter et al. |
| 2005/0131518 | A1 | 6/2005 | Hartley et al. |
| 2005/0177222 | A1 | 8/2005 | Mead |
| 2006/0095118 | A1 | 5/2006 | Hartley |
| 2006/0184228 | A1 | 8/2006 | Khoury |
| 2006/0229707 | A1 | 10/2006 | Khoury |
| 2007/0055350 | A1 | 3/2007 | Erickson et al. |
| 2007/0106368 | A1 | 5/2007 | Vonderwalde |

(56) References Cited

U.S. PATENT DOCUMENTS

| | | |
|---|---|---|
| 2007/0135818 A1 | 6/2007 | Moore et al. |
| 2007/0168013 A1 | 7/2007 | Douglas |
| 2007/0198078 A1 | 8/2007 | Berra et al. |
| 2007/0203566 A1 | 8/2007 | Arbefeuille et al. |
| 2008/0077226 A1 | 3/2008 | Ouellette et al. |
| 2008/0109066 A1 | 5/2008 | Quinn |
| 2008/0114444 A1 | 5/2008 | Yu |
| 2008/0147163 A1 | 6/2008 | Allen |
| 2008/0264102 A1 | 10/2008 | Berra |
| 2008/0281399 A1 | 11/2008 | Hartley et al. |
| 2009/0012597 A1 | 1/2009 | Doig et al. |
| 2009/0048663 A1 | 2/2009 | Greenberg |
| 2009/0125100 A1 | 5/2009 | Mead |
| 2009/0264988 A1 | 10/2009 | Mafi et al. |
| 2009/0306763 A1 | 12/2009 | Roeder et al. |
| 2009/0319022 A1 | 12/2009 | Hartley et al. |
| 2010/0030255 A1 | 2/2010 | Berra et al. |
| 2010/0049298 A1 | 2/2010 | Hamer et al. |
| 2010/0057186 A1 | 3/2010 | West et al. |
| 2010/0234932 A1 | 9/2010 | Arbefeuille et al. |
| 2011/0087318 A1 | 4/2011 | Daugherty et al. |
| 2011/0118821 A1 | 5/2011 | Brocker et al. |
| 2011/0172762 A1 | 7/2011 | Hartley et al. |
| 2011/0208288 A1 | 8/2011 | Arbefeuille et al. |
| 2011/0218607 A1 | 9/2011 | Arbefeuille et al. |
| 2011/0245906 A1 | 10/2011 | DiMatteo et al. |
| 2011/0257731 A1 | 10/2011 | Hartley et al. |
| 2011/0313503 A1 | 12/2011 | Berra et al. |
| 2012/0046728 A1 | 2/2012 | Huser et al. |
| 2012/0123464 A1 | 5/2012 | Rasmussen et al. |
| 2012/0245672 A1 | 9/2012 | Arbefeuille et al. |
| 2012/0271401 A1* | 10/2012 | Bruszewski ............... A61F 2/07 623/1.15 |
| 2012/0296414 A1 | 11/2012 | Hartley |
| 2012/0310324 A1 | 12/2012 | Benary et al. |
| 2013/0013053 A1 | 1/2013 | Hartley et al. |
| 2013/0079870 A1 | 3/2013 | Roeder et al. |
| 2013/0138199 A1 | 5/2013 | Ivancev et al. |
| 2013/0184806 A1 | 7/2013 | Arbefeuille et al. |
| 2013/0197627 A1 | 8/2013 | Jensen et al. |
| 2013/0211506 A1 | 8/2013 | Dake et al. |
| 2013/0268059 A1 | 10/2013 | Hagaman et al. |
| 2013/0282103 A1 | 10/2013 | Madjarov et al. |
| 2014/0039597 A9 | 2/2014 | Arbefeuille et al. |
| 2014/0135890 A9 | 5/2014 | Berra |
| 2014/0135892 A1 | 5/2014 | Arbefeuille et al. |
| 2014/0135896 A1 | 5/2014 | Arbefeuille et al. |
| 2014/0148890 A9 | 5/2014 | Ouellette et al. |
| 2014/0243952 A1 | 8/2014 | Parodi |
| 2014/0277340 A1 | 9/2014 | White et al. |
| 2014/0277370 A1 | 9/2014 | Brocker et al. |
| 2014/0288627 A1 | 9/2014 | Ouellette et al. |
| 2015/0173922 A1 | 6/2015 | Arbefeuille et al. |
| 2015/0202066 A1 | 7/2015 | Berra et al. |
| 2015/0272755 A1 | 10/2015 | Arbefeuille et al. |
| 2016/0045350 A1 | 2/2016 | Berra et al. |
| 2016/0081787 A1 | 3/2016 | Parodi et al. |
| 2016/0270901 A1 | 9/2016 | Berra et al. |
| 2016/0270936 A1 | 9/2016 | Berra et al. |
| 2016/0310301 A1 | 10/2016 | Moore et al. |
| 2016/0338867 A1 | 11/2016 | White et al. |
| 2017/0000600 A1 | 1/2017 | Berra et al. |
| 2017/0100232 A1 | 4/2017 | Arbefeuille et al. |
| 2017/0100271 A1 | 4/2017 | Arbefeuille et al. |
| 2017/0151076 A9 | 6/2017 | Arbefeuille et al. |
| 2017/0165090 A1 | 6/2017 | Arbefeuille et al. |
| 2017/0165091 A1 | 6/2017 | Arbefeuille et al. |
| 2017/0281332 A1 | 10/2017 | Lostetter et al. |
| 2017/0281382 A1 | 10/2017 | Lostetter et al. |
| 2017/0340433 A1 | 11/2017 | Berra |
| 2017/0340462 A1 | 11/2017 | Lostetter |
| 2018/0071123 A1 | 3/2018 | Arbefeuille |
| 2018/0110638 A1 | 4/2018 | Berra et al. |
| 2018/0140448 A1 | 5/2018 | Arbefeuille et al. |
| 2018/0206972 A1 | 7/2018 | Arbefeuille et al. |

FOREIGN PATENT DOCUMENTS

| | | |
|---|---|---|
| EP | 2 139 429 B1 | 6/2011 |
| EP | 1 765 222 B1 | 10/2012 |
| EP | 2 410 945 B1 | 11/2012 |
| EP | 1 983 933 B1 | 1/2013 |
| EP | 2 182 889 B1 | 9/2014 |
| EP | 2 331 013 B1 | 11/2014 |
| EP | 2 420 206 B1 | 1/2015 |
| EP | 2 450 006 B1 | 1/2015 |
| WO | WO 01/32103 A1 | 5/2001 |
| WO | WO 02/38085 A1 | 5/2002 |
| WO | WO 03/082153 A2 | 10/2003 |
| WO | WO 2005/023149 A2 | 3/2005 |
| WO | WO 2006/034276 A1 | 3/2006 |
| WO | WO 2006/113501 A1 | 10/2006 |
| WO | WO 2007/092276 A2 | 8/2007 |
| WO | WO 2007/123956 A2 | 11/2007 |
| WO | WO 2008/021557 A1 | 2/2008 |
| WO | WO 2009/020653 A1 | 2/2009 |
| WO | WO 2009/124124 A1 | 10/2009 |
| WO | WO 2010/005524 A2 | 1/2010 |
| WO | WO 2010/024879 A1 | 3/2010 |
| WO | WO 2010/105195 A2 | 9/2010 |
| WO | WO 2011/056638 A1 | 5/2011 |
| WO | WO 2013/071222 A1 | 5/2013 |
| WO | WO 2013/074990 A1 | 5/2013 |
| WO | WO 2013/154749 A1 | 10/2013 |
| WO | WO 2014/149022 A1 | 9/2014 |
| WO | WO 2016/049037 A1 | 3/2016 |
| WO | 2018031632 A1 | 2/2018 |

OTHER PUBLICATIONS

Browne, T.F., et al., "Endovascular and Surgical Techniques: A Fenestrated Covered Suprarenal Aortic Stent," *Eur J Vasc Endovasc Surg*, 18:445-449 (1999).

Chuter, T.A.M., et al., "Development of a Branched Stent-Graft for Endovascular Repair of Aortic Arch Aneurysms," *J Endovasc Ther*, 10:940-945 (2003).

Chuter, T.A.M., et al., "Modular Branched Stent Graft for Endovascular Repair of Aortic Arch Aneurysm and Dissection," *J Vasc Surg*, 38:859-863 (2003).

Funovics, M., "Branched Endografts for Aortic Arch Aneurysms—How Close Are We?," CIRSE 2011 Conference, Munich, Germany, Session No. 802.3 (Sep. 10-14, 2011).

Funovics, M., "TEVAR in the Ascending Aorta: A New Frontier for Endografting—Preliminary Results and Technology Transfer," Focus Meeting, Bolton Medical Inc., Barcelona, Spain (Oct. 2011).

Inoue, K., et al., "Aortic Arch Reconstruction by Transluminally Placed Endovascular Branched Stent Graft," *Circulation*, 100(Suppl II):II-316-II-321 (1999).

Inoue, K., et al., "Clinical Endovascular Placement of Branched Graft for Type B Aortic Dissection," *J Thorac Cardiovasc Surg*, 112:1111-1113 (1996).

Inoue, K., et al., "Transluminal Endovascular Branched Graft Placement for a Pseudoaneurysm: Reconstruction of the Descending Thoracic Aorta Including the Celiac Axis," *J Thorac Cardiovasc Surg*, 114:859-861 (1997).

Kinney, E.V., et al., "Repair of Mycotic Paravisceral Aneurysm with a Fenestrated Stent-Graft," *J Endovasc Ther*, 7:192-197 (2000).

Lioupis, C., et al., "Treatment of Aortic Arch Aneurysms with a Modular Transfemoral Multibranched Stent Graft: Initial Experience," *European Journal of Vascular and Endovascular Surgery*, 43:525-532 (2012).

Martinelli, L., "Partial Ascending Aorta and Total Arch Reconstruction with Bolton Medical Branched Thoracic Endograft," Cardiovasular Surgery Meeting, Bologna, Italy (Nov. 14-15, 2011).

Ouriel, K. and Clair, D.G., "Branched Device to Preserve Hypogastric Arterial Flow with Thoracoabdominal Aneurysm Repair," *J Vasc Surg*, 37:481 (2003).

Simring, D., et al., "Total Endovascular Repair of the Arch: Branched Endografting Makes it Easy," *Tecnicas Endovasculares*, 14(1):3712-3716 (2011).

(56) References Cited

OTHER PUBLICATIONS

Wisselink, W., et al., "Endoluminal Repair of Aneurysms Containing Ostia of Essential Branch Arteries: An Experimental Model," *J Endovasc Surg*, 6:171-179 (1999).

Notification of Transmittal of the International Search Report and the Written Opinion of the International Searching Authority, or the Declaration, International Application No. PCT/US2012/065622, Titled: "Device and Method for Aortic Branched Vessel Repair," dated Mar. 1, 2013 (14 pages).

Notification of Transmittal of the International Search Report and the Written Opinion of the International Searching Authority, International Application No. PCT/US2012/064612, Titled: "Universal Endovascular Grafts," dated Apr. 2, 2013 (10 pages).

Notification Concerning Transmittal of International Preliminary Report on Patentability, International Application No. PCT/US2012/064612, Titled: "Universal Endovascular Grafts," dated May 22, 2014 (7 pages).

Notification Concerning Transmittal of International Preliminary Report on Patentability, International Application No. PCT/US2012/065622, Titled: "Device and Method for Aortic Branched Vessel Repair," dated May 30, 2014 (7 pages).

Non-Final Office Action, U.S. Appl. No. 13/788,724, dated Apr. 28, 2015 (14 pages).

Office Action, U.S. Appl. No. 14/272,818, Titled: "Universal Endovascular Grafts," dated Sep. 9, 2015 (14 pages).

Notification of Transmittal of the International Search Report and the Written Opinion of the International Searching Authority, International Application No. PCT/US2015/051470, entitled: "Vascular Repair Devices and Methods of Use," dated Dec. 4, 2015 (15 pages).

Office Action, U.S. Appl. No. 14/272,818, dated Mar. 17, 2016 (14 pages).

Final Office Action, U.S. Appl. No. 13/788,724, dated Apr. 21, 2016 (32 pages).

Office Action, U.S. Appl. No. 14/272,818, dated Aug. 25, 2016 (11 pages).

Notice of Allowance, U.S. Appl. No. 13/788,724, dated Nov. 28, 2016 (17 pages).

Office Action, U.S. Appl. No. 14/272,818, dated Feb. 1, 2017 (9 pages).

Notification Concerning Transmittal of International Preliminary Report on Patentability, International Application No. PCT/US2015/051470, entitled: "Vascular Repair Devices and Methods of Use," dated Apr. 6, 2017 (10 pages).

Office Action, U.S. Appl. No. 14/861,479, dated May 1, 2017 (52 pages).

\* cited by examiner

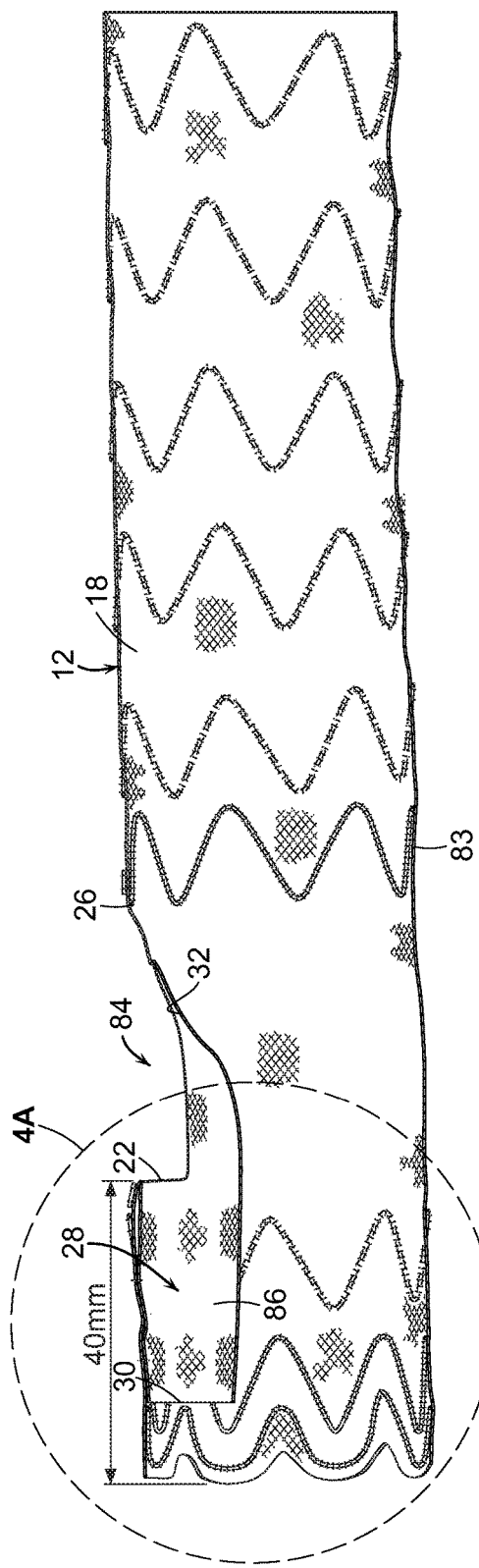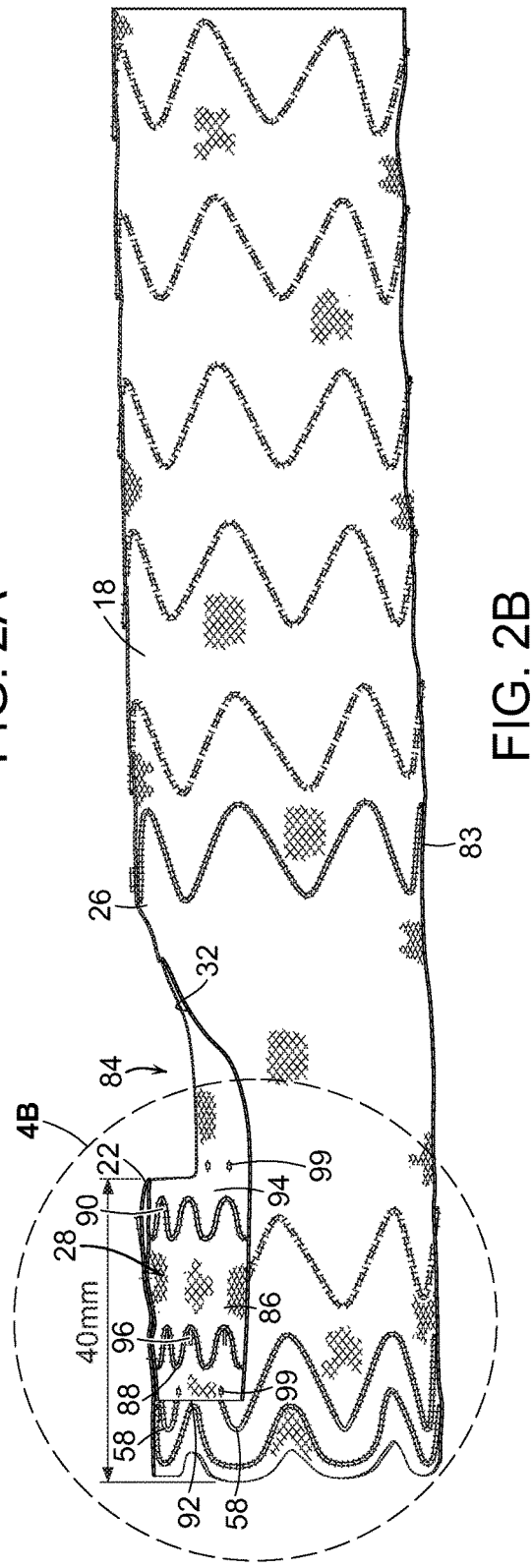
FIG. 2A
FIG. 2B

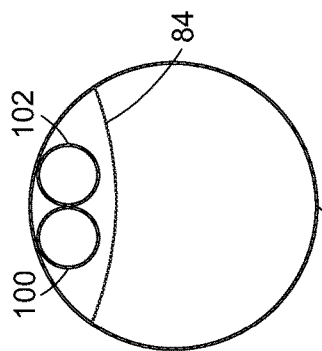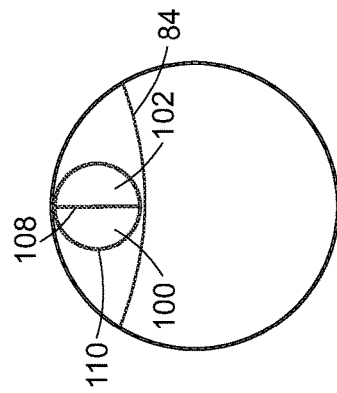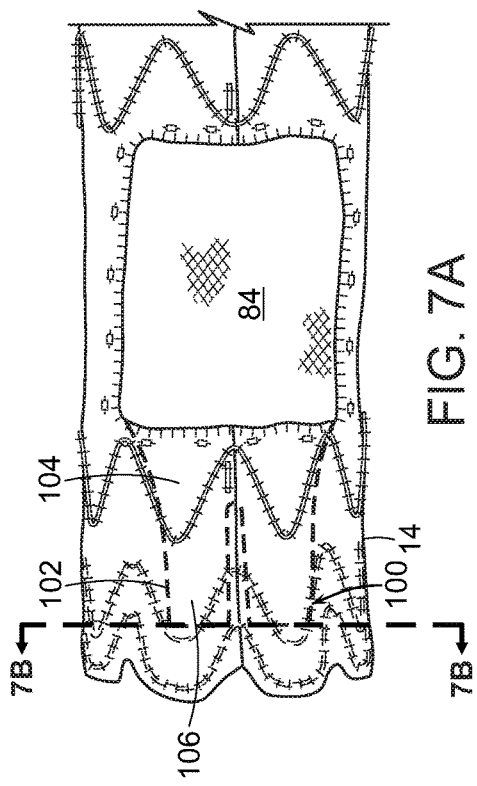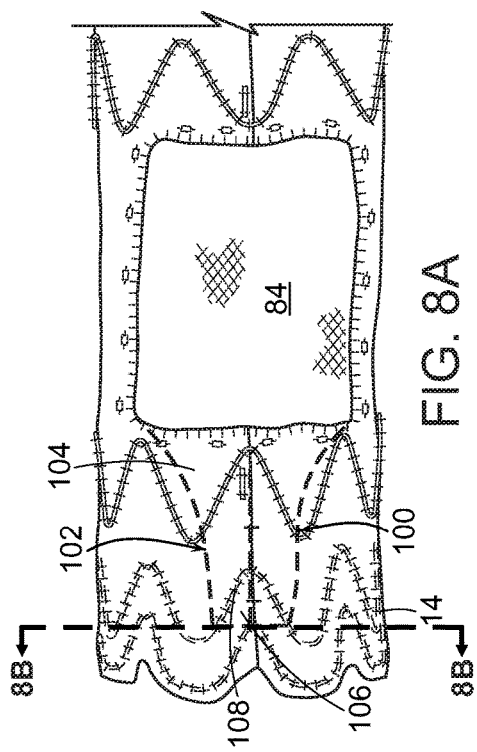

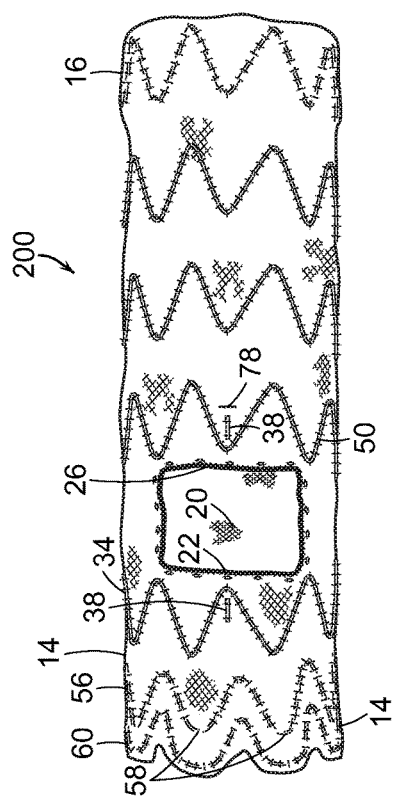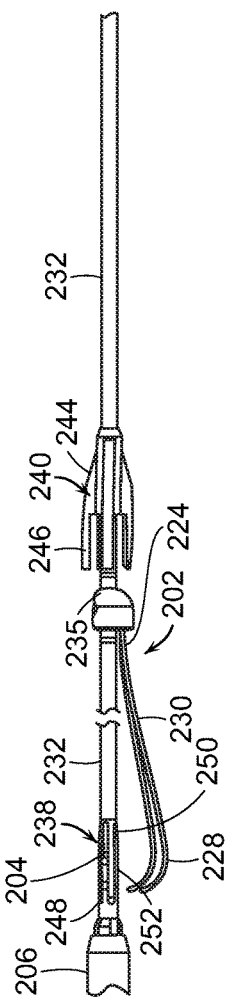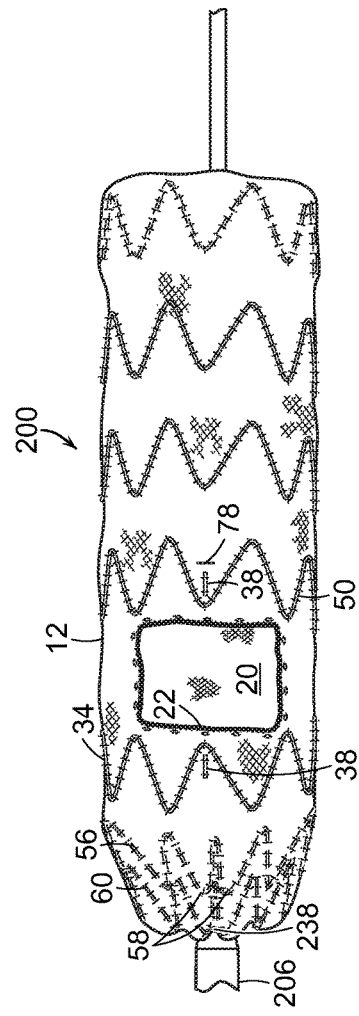

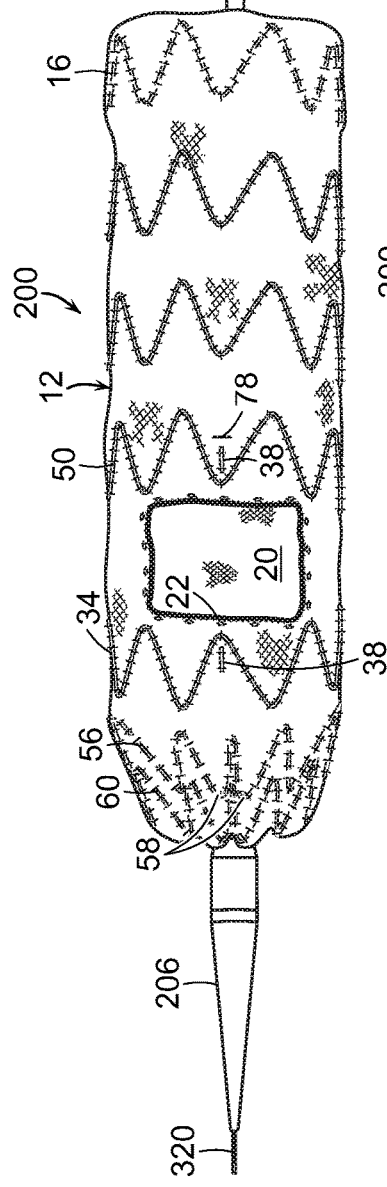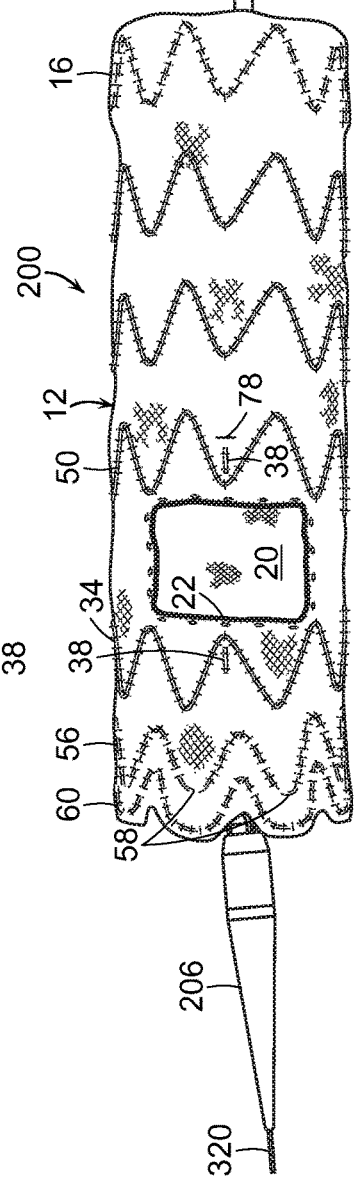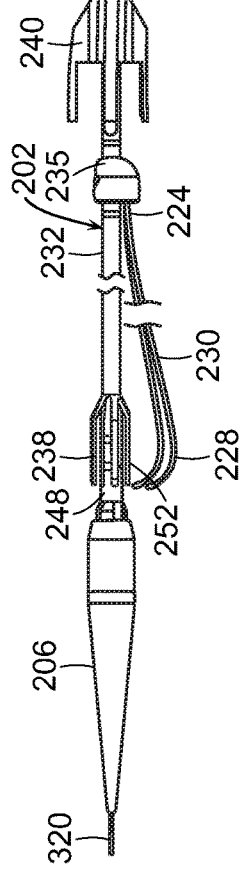
FIG. 16D
FIG. 16E
FIG. 16F

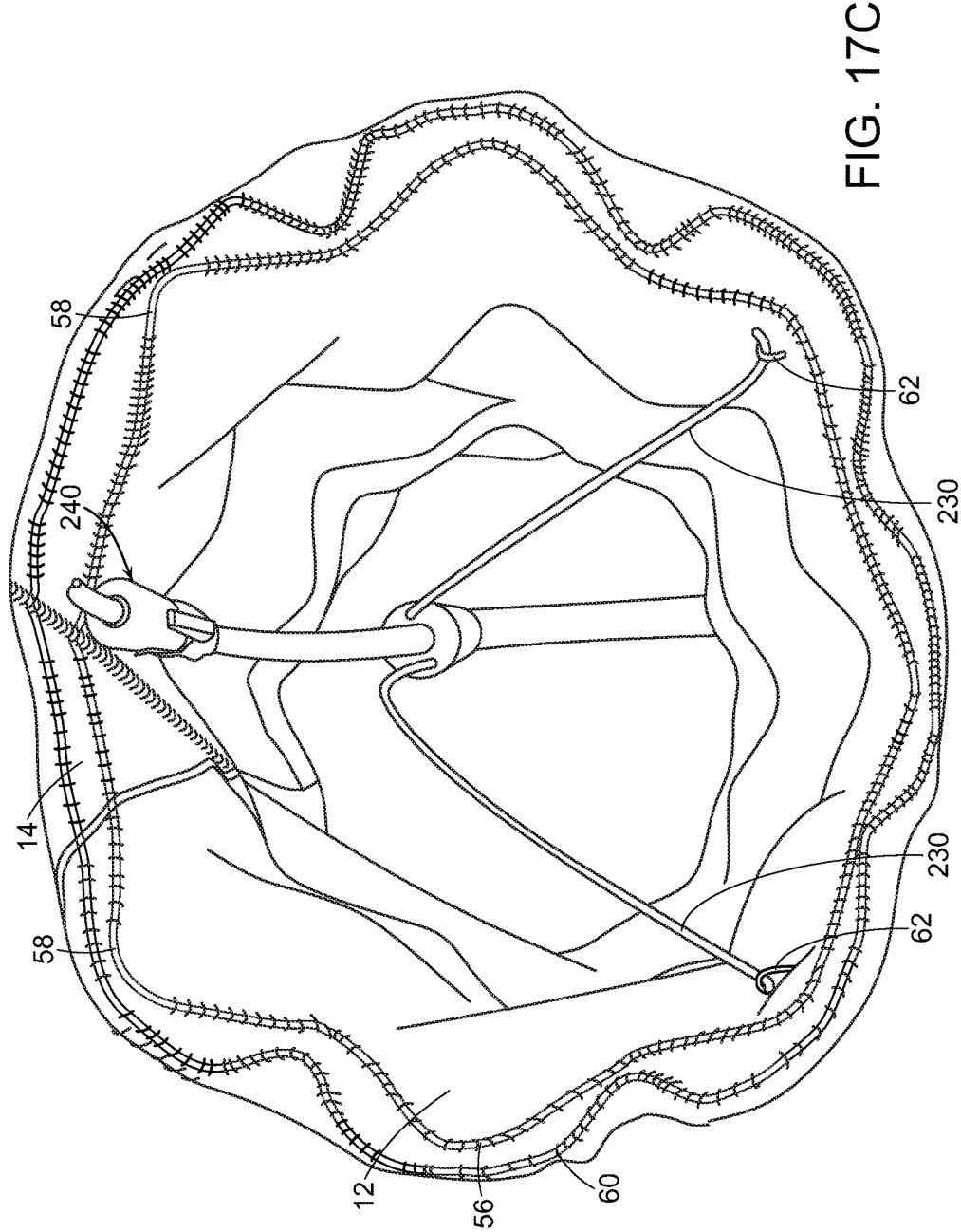

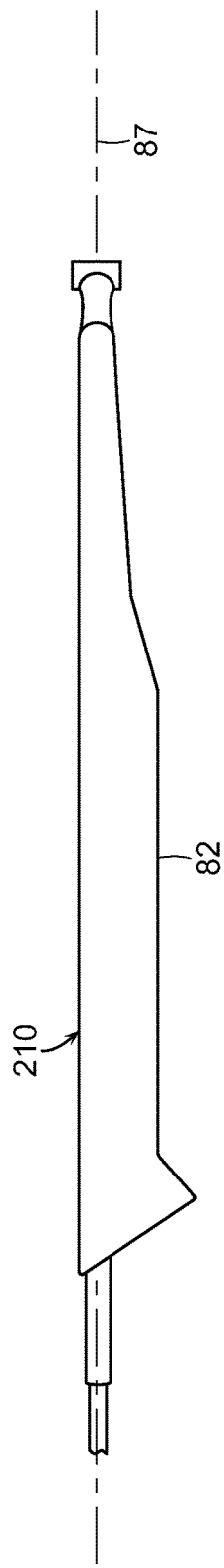
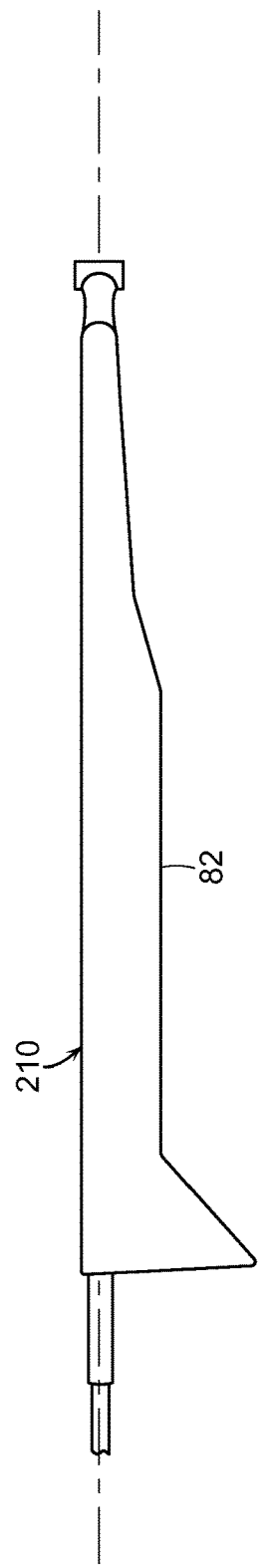
FIG. 19A
FIG. 19B

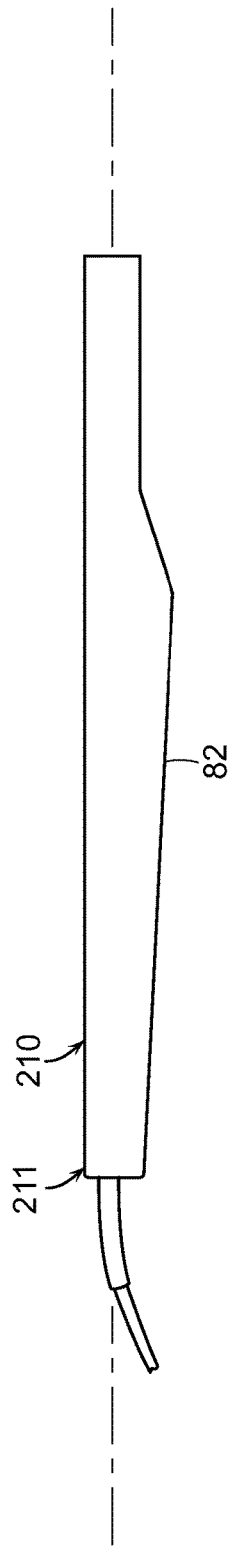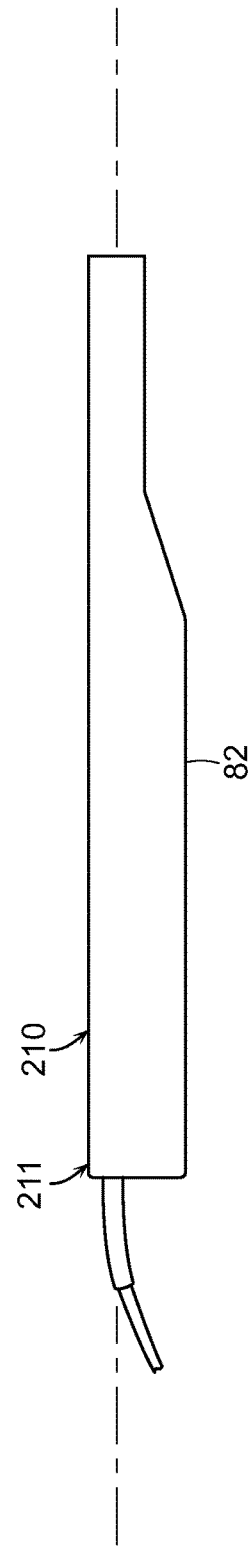
FIG. 21A
FIG. 21B

METHOD FOR AORTIC BRANCHED VESSEL REPAIR

RELATED APPLICATIONS

This application is a divisional of U.S. patent application Ser. No. 13/788,724, filed Mar. 7, 2013, which is a continuation of International Application No. PCT/US2012/065622, filed on Nov. 16, 2012, which claims the benefit of U.S. Provisional Application No. 61/560,517, filed on Nov. 16, 2011. The entire teachings of the above applications are incorporated herein by reference.

BACKGROUND OF THE INVENTION

Aortic aneurysms are life-threatening conditions. Surgical interventions used to treat aortic aneurysms include endovascular repair by transluminal placement of one or more endografts across the longitudinal extent of the lesion. The endograft is placed in the aorta with the intention of bridging the aneurysmal sac to exclude it from the high-pressure of aortic blood flow, which can permit remodeling of the aortic wall in and around the aneurysm site. In certain regions of the aorta accurate placement of the endograft is critical to maintain blood flow to vessels branching from the aorta to minimize compromised blood flow to organs. For example, currently, if aortic devices are placed within the aortic arch in a manner that offsets the aperture for the left carotid artery, the artery can be occluded, which can result in ischemia to the brain. Most surgical methods of treating aneurysms at or near the aortic arch generally involve sternotomy or thoracotomy and may require cardio-pulmonary bypass, often resulting in high morbidity rates. Thus, there is a need to develop new and useful devices and methods of treating aortic aneurysms by endovascular methods.

SUMMARY OF THE INVENTION

The present invention relates to vascular repair systems, delivery systems and methods of using the delivery systems and its components to treat aortic vascular damage, in particular, vascular damage associated with aortic disease, such as, aneurysms, penetrating atherosclerotic ulcers and dissection.

In an embodiment, the invention is an aortic graft assembly that includes a tubular aortic component having a proximal end and a distal end connected by a wall of the tubular aortic component, the wall defining a wall aperture that is between the proximal and distal ends. The aperture has a proximal end that extends perpendicular to a major longitudinal axis of the tubular aortic component when viewed orthogonally to the major longitudinal axis. A tunnel graft is connected to the wall of the tubular aortic component and extends from the wall aperture toward the proximal end of the tubular aortic component. The tunnel graft has a proximal end and a distal end, the distal end being at the wall aperture of the tubular aortic component. A proximal stent abuts the proximal end of the aperture, and a distal stent abuts a distal end of the aperture.

In yet another embodiment, the invention is an aortic graft assembly, comprising a tubular aortic component that includes a proximal end and a distal end connected by a wall of the tubular aortic component, the wall defining a wall aperture that is between the proximal and distal ends, the wall aperture having a proximal end and a distal end, the proximal end of the wall aperture extending perpendicular to a major longitudinal axis of the tubular aortic component when viewed orthogonally to the major longitudinal axis; a tunnel graft connected to the wall of the tubular aortic component and extending from the wall aperture toward the proximal end of the tubular aortic component, the tunnel graft having a proximal end and a distal end, the distal end being at the wall aperture of the tubular aortic component; a proximal stent that supports the proximal end of the tubular aortic component; a distal stent that supports the distal end of the tubular aortic component; a clasping stent at the proximal end of the tubular aortic component, the clasping stent including at least two exposed proximal apices proximate to the proximal end of tubular component and attached to an interior wall of the tubular aortic component; and a crown stent between the clasping stent and the proximal end of the tubular aortic component, the crown stent attached to an interior surface of the tubular aortic component.

In a further embodiment, the invention is an aortic graft assembly, comprising a tubular aortic component that includes a proximal end and a distal end connected by a wall of the tubular aortic component, the wall defining a wall aperture that is between the proximal and distal ends, the wall aperture having a proximal end and a distal end, the proximal end of the wall aperture extending perpendicular to a major longitudinal axis of the tubular aortic component when viewed orthogonally to the major longitudinal axis; a tunnel graft connected to the wall of the tubular aortic component and extending from the wall aperture toward the proximal end of the tubular aortic component, the tunnel graft having a proximal end and a distal end, the distal end being at the wall aperture of the tubular aortic component; a proximal stent that abuts the proximal end of the tubular aortic component; a distal stent that supports the distal end of the tubular aortic component; an abutting distal stent that includes at least one proximal apex that abut the distal end of the wall aperture; a clasping stent at the proximal end of the tubular aortic component, the clasping stent including at least two exposed proximal apices proximate to the proximal end of tubular component and attached to an interior wall of the tubular aortic component; and a crown stent between the clasping stent and the proximal end of the tubular aortic component, the crown stent attached to an interior surface of the tubular aortic component.

In another embodiment, the invention is a method for implanting a prosthesis, including delivering a tubular aortic component defining a wall aperture through an aorta of a patient to an aneurysm site of the patient, the tubular aortic component being radially and releasably constrained by a distal clasp at a distal end of an outer control tube of a delivery device, and releasably attached by a retention component to a proximal clasp at the outer control tube proximal to the proximal clasp, the tubular aortic component further supported by a control catheter of the delivery device extending within the outer control tube. The wall aperture is aligned over at least one vessel ostium at the aneurysm site of the patient. The outer tube is retracted, thereby releasing the tubular aortic component from the distal and proximal clasps, thereby deploying the tubular aortic component at the aneurysm site.

In an additional embodiment, the invention is a method for implanting a prosthesis, comprising the steps of delivering a tubular aortic component defining a wall aperture through an aorta to an aneurysm site of a patient, the tubular aortic component being radially and releasably constrained by a distal clasp at a distal end of an outer control tube of a delivery device, and releasably attached by a retention component to a proximal clasp at the outer control tube proximal to the proximal clasp, the tubular aortic component further supported by a control catheter of the delivery device extending within the outer control tube; aligning the wall aperture over at least one vessel ostium at the aneurysm site of the patient; retracting the outer control tube, thereby releasing the tubular aortic component from the distal and proximal clasps, thereby deploying the tubular aortic component at the aneurysm site in the patient, wherein at least one supporting wire extends from the control tube, said supporting wire extending through a suture loop inside the proximal end of the tubular aortic component to thereby prevent collapse of the proximal end of the tubular component during deployment. The method can further includes the step of partially retracting an inner sheath from around the tubular aortic component, whereby the supporting wire at least partially restricts longitudinal movement of the proximal end of the tubular aortic component until the proximal end of the tubular aortic component is secure within the aorta, to thereby prevent collapse of the proximal end of the tubular aortic component at an inferior portion of the aorta, wherein the inner sheath is releasably secured to a distal end within a cavity defined by a proximal end of the nose cone, wherein the steps of the method include partially retracting an inner sheath around the tubular aortic component to release the distal end of the inner sheath from the nose cone and thereby cause partial deployment of the tubular aortic component; partially retracting the control catheter to thereby release the clasping stent from the distal apex clasp and the retention component from the proximal clasp; further retracting the control catheter to at least partially retract the nose cone to within the tubular aortic component while retaining the suture loops on the supporting wires; advancing the tubular aortic component to a final position in the aorta of the patient spanning the aneurysm; fully retracting the inner sheath from the tubular aortic component; and fully retracting the nose cone and supporting wires to release the suture loops from the supporting wires, thereby fully deploying the tubular aortic component within the aorta of the patient.

In an embodiment, a stent defining the aperture permits blood flow into the ostium of the target vessel, unlike other systems that rely on a narrowing or dog-bone shape of the body of the tubular aortic component of an aortic graft system to permit blood flow outside and around the tubular graft component if the surgeon is unable to align the aperture with the ostium of the target vessel.

The aortic graft assembly of the invention does not require precise radial or longitudinal alignment in the aorta and permits approximate alignment, which is beneficial in reducing the manipulation of the aortic arch and resulting stroke in the patient. The claimed systems can be fully deployed before the surgeon completes the endovascular procedure by deployment of the first tunnel or second tunnel graft, unlike current aortic components that are in a "dog-bone" configuration to guard against unintentional obstruction of the target ostium. The delivery device employed with the graft assembly aids in proper alignment of the assembly in the aorta by, for example, use of a curved guidewire catheter, proximal clasp and distal clasp.

The aortic assembly systems and methods of the invention can be employed to treat aortic aneurysms, such as aortic aneurysms at, near or around the arch of the aorta, or branches from the abdominal aorta (e.g., celiac artery, superior mesenteric artery and renal arteries). The aortic assembly systems of the invention have a relatively large aperture tapered into a tunnel graft that provides the surgeon with a relatively large margin of error in placement of the system, facilitates canulation and permits alignment of a single aperture for at least one blood vessel. Aortic assembly systems of the invention that include a tunnel graft having one aperture extending proximally with two openings permit for easy alignment in the aorta, particularly in regions of the aorta that branch to peripheral and major vessels. The size of the aperture allows blood to flow to target vessels during the procedure. The aortic graft assembly of the invention generally does not restrict blood flow acutely or chronically, in part, because of a relatively large diameter of the tunnel graft and the stent or stents supporting the tunnel graft.

Barbs in the interior of the tunnel grafts of the branched graft assembly have the advantage of securing connection of the tubular component to the tunnel graft. The telescoping ability of the graft assembly systems of the invention, for example, the length and different configurations of the tunnel graft, allow the tubular component to be positioned in-situ to ensure maximum use of a "landing zone" inside the target vessel. A relatively long tunnel length can ensure adequate overlap with the tubular component into the tunnel grafts to ensure a sufficient seal.

The delivery device of the invention also has the advantage of allowing the proximal end of the stent graft to be aligned perpendicular to the center line axis of the "landing zone." This is of key concern when the landing zone is in Zone 0 (FIGS. 15, 16, 17) of the ascending aorta. When landing in this area much care must be taken to avoid accidental coverage of the coronary arteries, typically the left coronary artery.

Thus, the aortic graft assembly, delivery systems, and methods of the invention can be used to treat various aortic pathologies, including aortic aneurysms, penetrating atherosclerotic ulcers, dissections and, therefore, avoid complications and death consequent to life-threatening vascular conditions.

BRIEF DESCRIPTION OF THE DRAWINGS

FIGS. 2A and 3A represent cross sectional views of the aortic assembly system of the invention, shown in FIG. 1A, taken along line 2A.

FIGS. 2B and 3B represent a longitudinal view of FIGS. 2A and 3A of an aortic assembly system of the invention.

FIGS. 7A and 8A represent additional embodiments of an aortic assembly system of the invention.

FIGS. 7B and 8B represent additional embodiments of an aortic assembly system of the invention taken along lines 7B and 8B of FIGS. 7A and 8A, respectively.

FIGS. 16A-16F are a representation of one embodiment of an aortic assembly system of the invention of one embodiment of a delivery system of the invention.

FIGS. 17A-17C are side, cross-sectional and perspective views of one embodiment of the invention, respectively.

FIGS. 19A and 19B represent alternative embodiments of an inner sheath of an embodiment of a delivery system of the invention.

FIGS. 21A and 21B represent additional alternative embodiments of an inner sheath of an embodiment of a delivery system of the invention.

DETAILED DESCRIPTION OF THE INVENTION

Figure 1A:
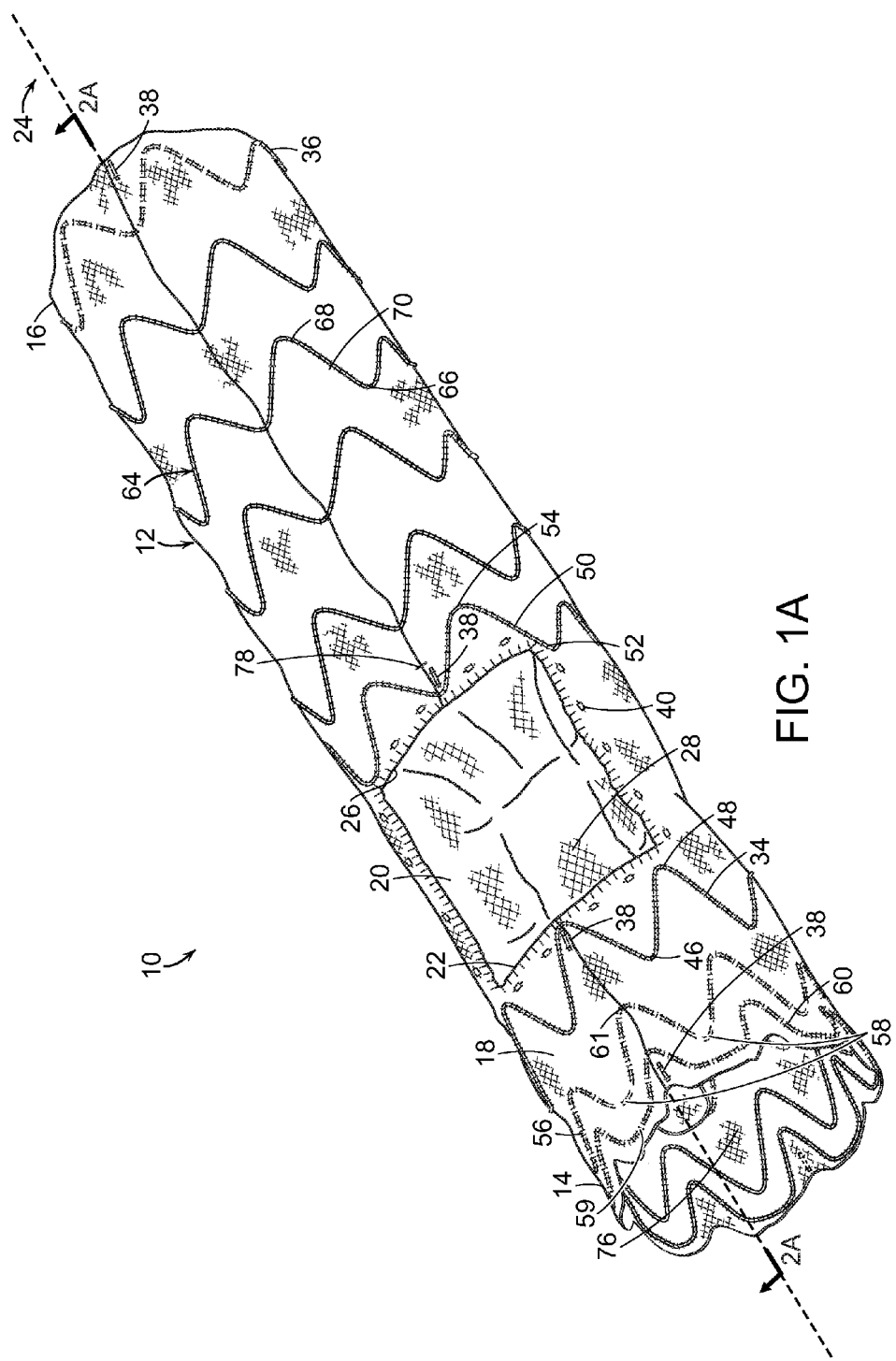
FIGS. 1A, 1B and 1C represent an embodiment of an aortic assembly system of the invention.

The features and other details of the invention, either as steps of the invention or as combinations of parts of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

"Proximal" means, when reference is made to a delivery system or a component of a delivery system, such as an apex clasp and a nose cone, closest to the clinician using device. Likewise, "distal" means, when reference is made to a delivery system or a component of a delivery system, such as an apex clasp and a nose cone, away from the clinician using the device.

When reference is made to a prosthesis to be delivered, such as an aortic graft assembly, tubular aortic component, tunnel graft, branch graft and stent, the word "proximal" means that portion of the prosthesis or component of the prosthesis that is towards the heart of the patient and "distal" means that portion of the prosthesis or component of the prosthesis that is away from the heart of the patient. For clarity, the word "proximate" means close to as opposed to "proximal" or "distal."

Aortic graft assemblies of the invention can be implanted, for example, by transfemoral access. Tubular branch components can be implanted, for example, by supraaortic vessel access (e.g., brachial artery), or by transfemoral or transapical access.

The invention is generally directed to an aortic graft assembly and a method for deploying the aortic graft assembly. The invention is also directed to methods of implanting at least one tubular branch graft into a patient and the aortic graft assembly. In one embodiment of the aortic graft assembly of the invention, represented in FIG. 1A through FIG. 1C, aortic graft assembly 10 includes tubular aortic component 12 having proximal end 14 and distal end 16 connected by wall 18. Wall 18 defines wall aperture 20 that is between proximal end 14 and distal end 16. Wall aperture 20 has proximal end 22 that extends perpendicular to a major longitudinal axis 24 of tubular aortic component 12 when viewed orthogonally to major longitudinal axis 24. Wall aperture 20 also defines distal end 26 of wall aperture 20.

Tunnel graft 28, shown, for example, in FIGS. 2A, 2B, 3A, 3B, 4A and 4B is connected to wall 18 of tubular aortic component 12 and extends from wall aperture 20 toward proximal end 14 of the tubular aortic component 12. Tunnel graft 28 includes proximal end 30 and distal end 32. Distal end 32 of tunnel graft 28 is at wall aperture 20 of tubular aortic component 12.

Referring back to FIGS. 1A-1C, proximal stent 34 supports proximal end 14 of tubular aortic component 12. Distal stent 36 supports distal end 16 of tubular aortic component 12. Similarly, distal stent 36 can be attached to an interior wall to tubular aortic component 12.

Optionally, radiopaque markers 38 are located along a line parallel to major longitudinal axis 24 of tubular aortic component 12. In one embodiment, radiopaque marker 38 is at a proximal apex of wall aperture distal stent 50 abutting wall aperture 20. Another radiopaque marker is at a distal apex 48 of proximal stent 34. Further, radiopaque marker 38 is at least one of proximal end 14 and distal end 16 of tubular aortic component 12. Also optionally, radiopaque markers 40 extend about the circumference of wall aperture 20 at tubular aortic component 12. Radiopaque markers 38, 40 can be made of any suitable material such as platinum, iridium, gold, etc. Examples of radiopaque markers are described in the U.S. Pat. No. 8,062,345 and U.S. Published Patent Application No.: US 2010/0030255, the entire teachings of which are incorporated herein by reference.

Figure 1B:
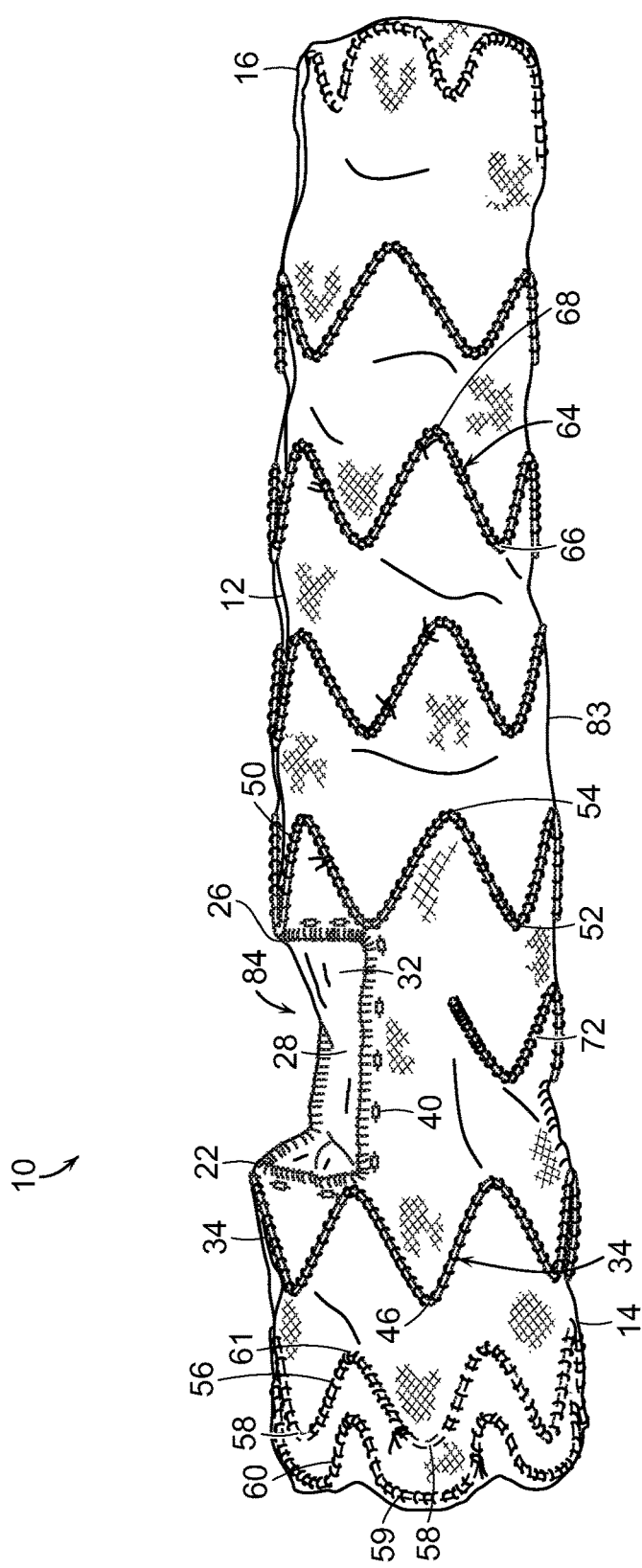
Figure 1C:
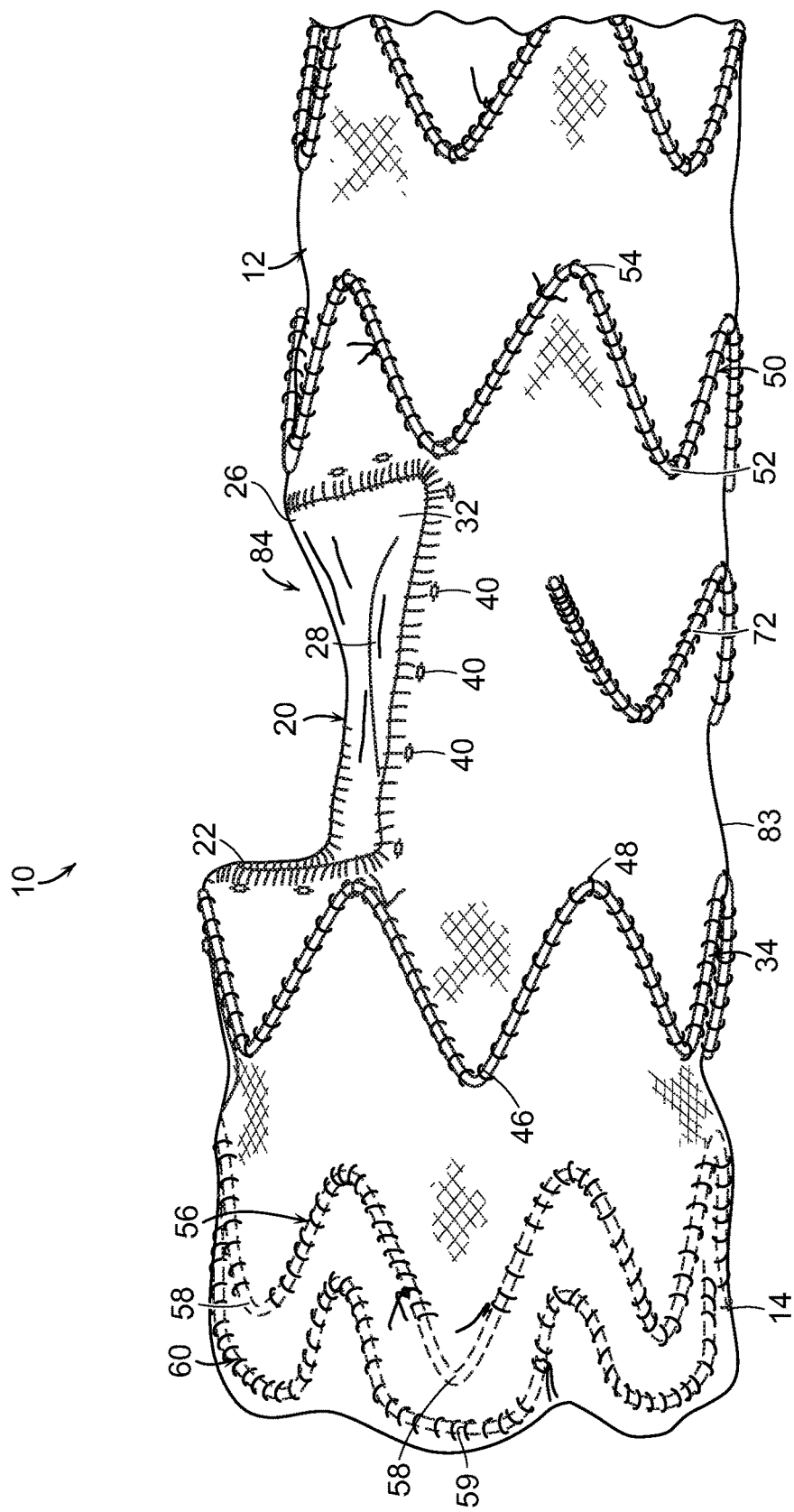

Proximal stent 34 in one embodiment, shown in FIGS. 1A, 1B and 1C, includes proximal apices 46 and distal apices 48. In one embodiment, at least a portion of distal apices 48 abut proximal end 22 of wall aperture 20. Wall aperture distal stent 50 includes proximal apices 52 and distal apices 54, a portion of proximal apices 52 of wall aperture distal stent 50 abut distal end 26 of wall aperture 20. Clasping stent 56 at proximal end 14 of tubular aortic component 12 includes at least two exposed proximal apices 58 proximate to proximate end 14 of tubular aortic component 12. In one embodiment, clasping stent 56 is attached to an interior wall of tubular aortic component 12.

Figure 5:
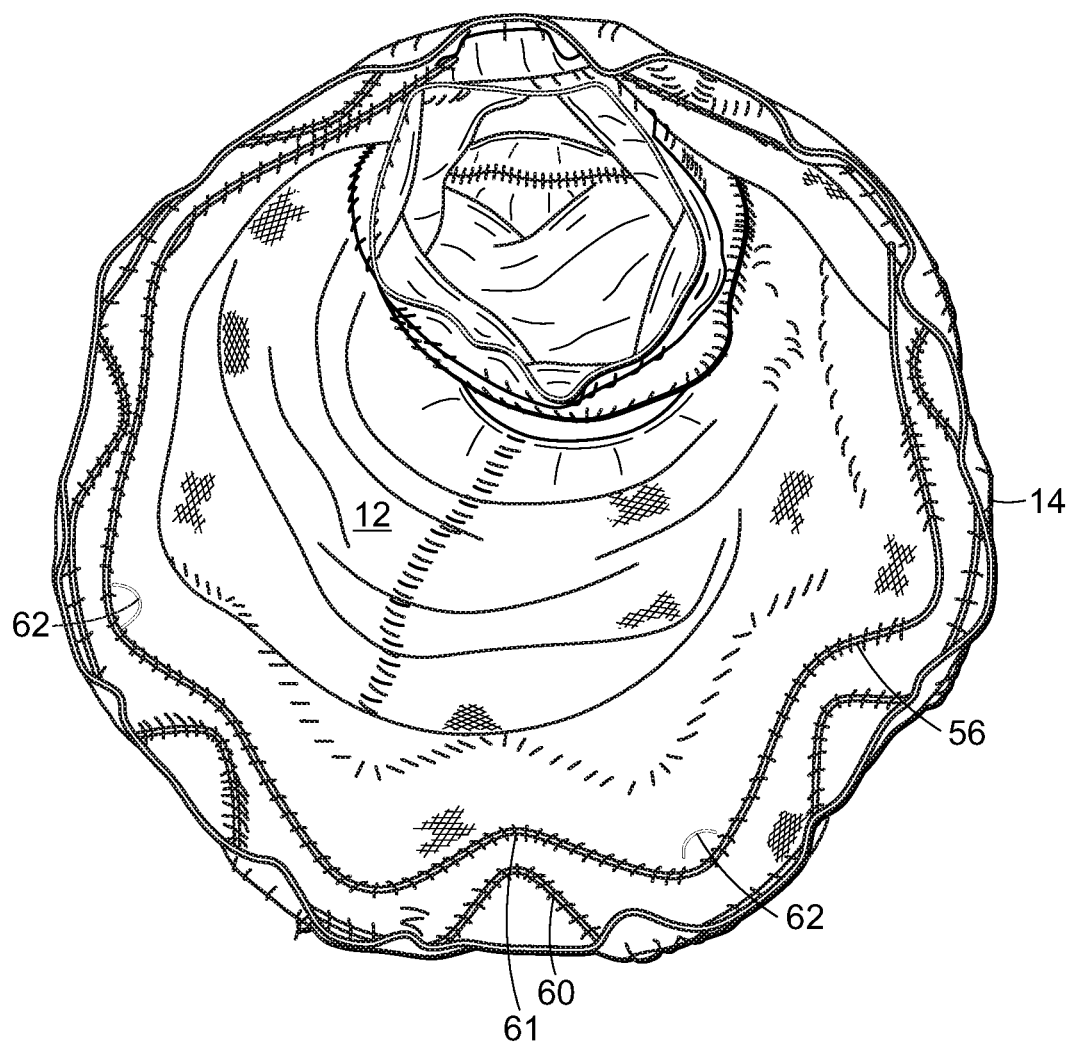
FIG. 5 is a perspective view into the proximal end of one embodiment of the invention.

Crown stent 60 is located between clasping stent 56 and proximal end 14 of tubular aortic component 12. As can be seen in FIG. 5, at least two support wire sutures 62 are located within tubular aortic component 12 at proximal end 14 of tubular aortic component 12, distal to proximal apices 58 of clasping stent 56. Support wires sutures 62 are separated by at least one distal apex 61 of clasping stent 56. In one embodiment, proximal apices 59 of crown stent 60 are blunted, as shown in FIG. 1A. Crown stent 60 and clasping stent 56 can be nested, as shown in FIG. 1A. Crown stent 60 and clasping stent 56 are attached to interior wall 76 of tubular aortic component 12.

At least one stent 64 is located at tubular aortic component 12 between proximal stent 34 and distal stent 36. At least a portion of stents 64 include proximal apices 66 and distal apices 68 connected by struts 70. At least one partial stent 72 is located at tubular aortic component 12 between stents 34, 50 abutting proximal 22 and distal 26 ends of wall aperture 20, respectively, as shown in FIGS. 1B and 1C.

Stents employed in the invention are constructed of a suitable material. In one embodiment, the stents employed by the invention include a suitable shape memory alloy, such as nitinol. Further description of suitable materials for construction of stents for use in the invention can be found in U.S. Pat. Nos. 7,763,063 and 8,062,345, the teachings of which are incorporated herein by reference in their entirety.

In one embodiment, the arc length of proximal end 22 of wall aperture 20 is equal to or less than one-half the circumference of tubular aortic component 12. Examples of suitable arc lengths of proximal end 22 of wall aperture 20 include arc lengths equal to one member selected from the group consisting of about 6 mm, about 8 mm, about 10 mm, about 12 mm or about 14 mm. In one embodiment, a longitudinal length of wall aperture 20 is equal to or less than about 90 mm. In another embodiment, the longitudinal length of wall aperture 20 is equal to or greater than about 14 mm.

Figure 3A:
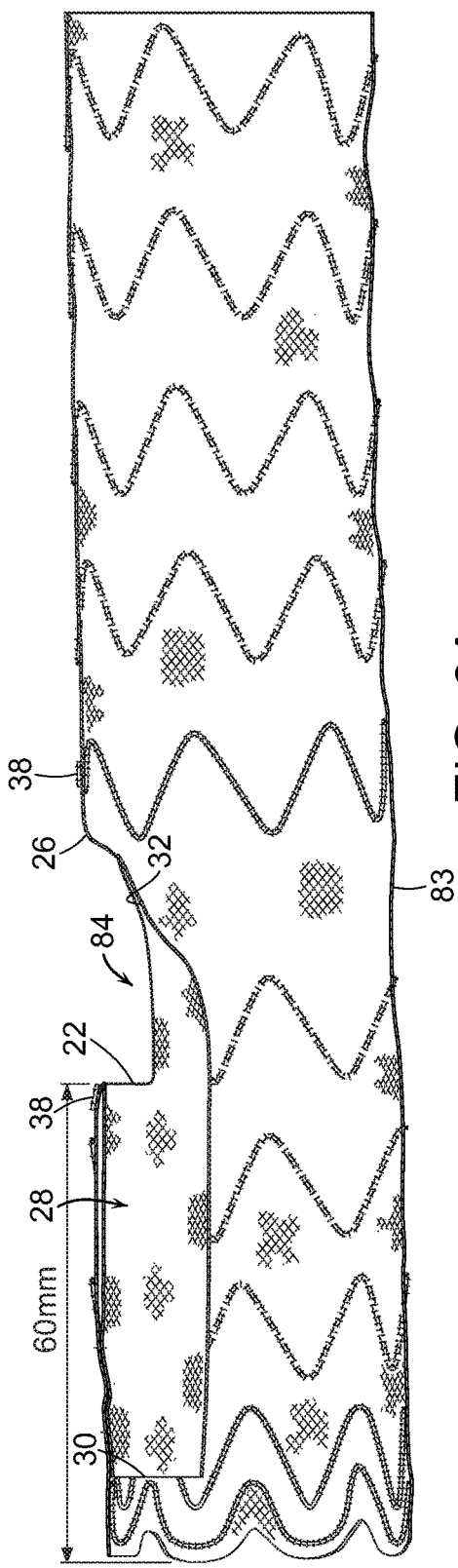
Figure 3B:
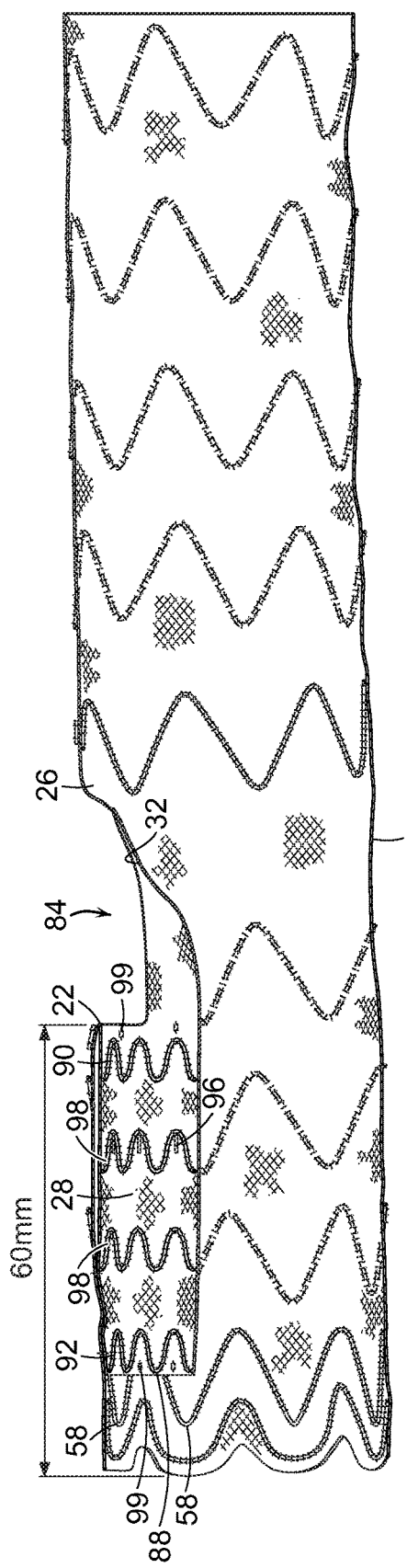

Referring to FIGS. 2A, 2B, 3A and 3B, the distance between proximal end 22 of wall aperture 20 and proximal end 14 of tubular aortic component 12 can be in a range of between about 10 mm and about 80 mm. In a typical embodiment, the distance between proximal end 22 of wall aperture 20 and proximal end 14 of tubular aortic component 12 is one member selected from the group consisting of about 20 mm, about 40 mm, about 60 mm, about 80 mm or about 90 mm. In one embodiment, the distance between proximal end 22 of wall aperture 20 and proximal end 12 of tubular aortic component 12 is about 40 mm, as shown in FIGS. 2A and 2B. In another embodiment, the distance between proximal end 22 of wall aperture 20 and proximal end 14 of tubular aortic component 12 is about 60 mm, as shown in FIGS. 3A and 3B.

In one embodiment, shown in FIG. 1A, retention component 78 is located at tubular aortic component 12 distal to wall aperture 20 and within tubular aortic component 12 (only external portion of retention component 78 is shown in FIG. 1A). In one embodiment, retention component is a suture loop. In another embodiment, retention component 78 is at least one of a magnet or a stent apex. In still another embodiment, retention component 78 is radiopaque. In one embodiment, retention component 78 is at a proximal apex 52 of stent 50 abutting distal end 26 of wall aperture 20.

Figure 6:
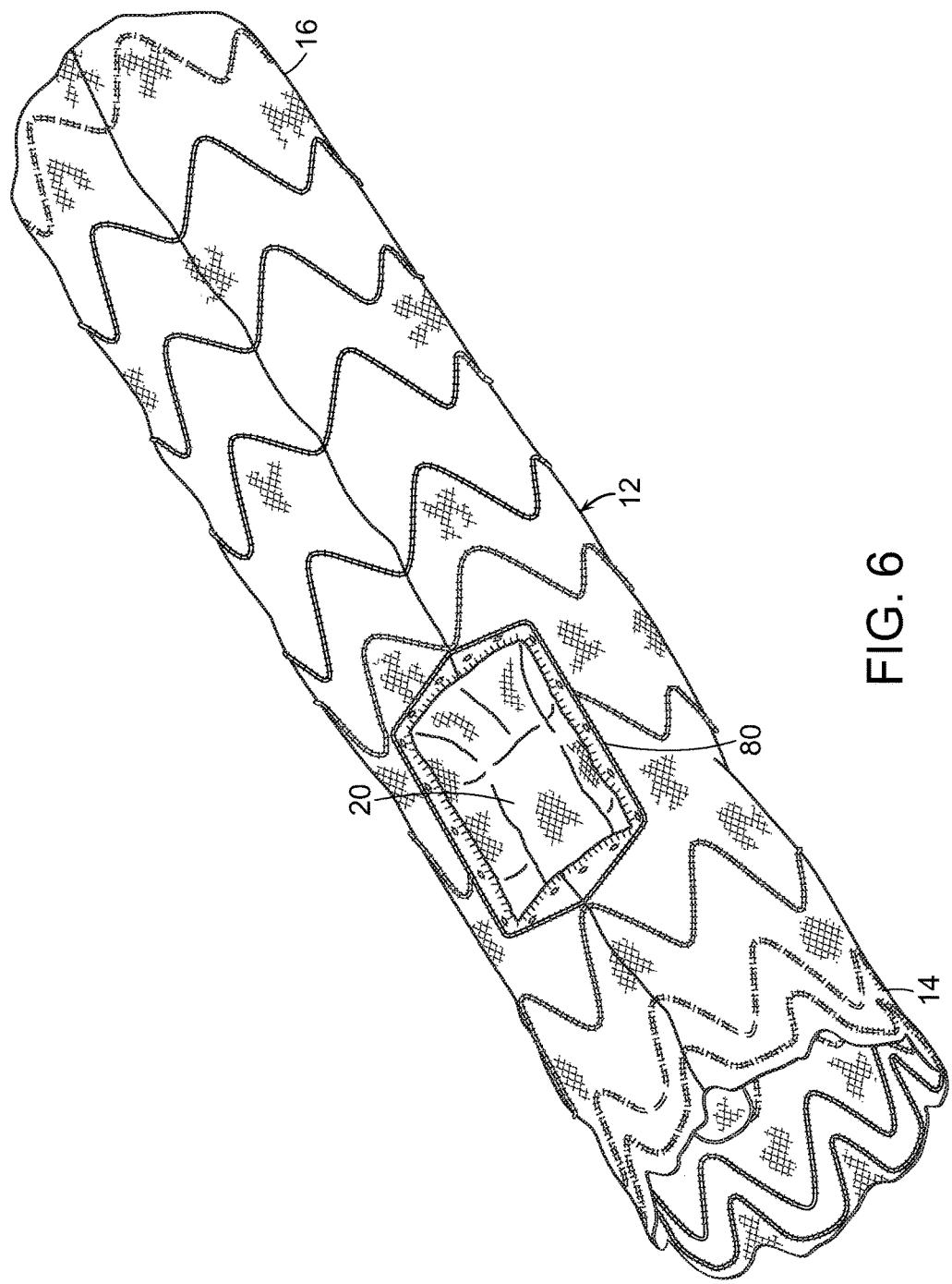
FIG. 6 represents another embodiment of an aortic assembly system of the invention.

In another embodiment, shown in FIG. 6, circumferential stent 80 is located at tubular aortic component 12 and surrounds wall aperture 20. In one embodiment, a circumferential stent 80 surrounding wall aperture 20 defines, at least in part, wall aperture 20. In one embodiment, the diameter of proximal end 14 of tubular aortic component 12 is greater than the diameter of distal end 16 of tubular aortic component 12, as shown in FIG. 1B.

In one embodiment, shown in FIGS. 7A, 8A, 9A and 10A, the interface between tubular aortic component 12 and wall aperture 20, when viewed orthogonally to major longitudinal axis 24 of tubular aortic component 12 is a polygon, such as is shown in the referenced figures, a polygon having four sides. In various embodiments, the polygon can be a square, a rectangle, a parallelogram, or a rhombus (not shown).

Figure 11:
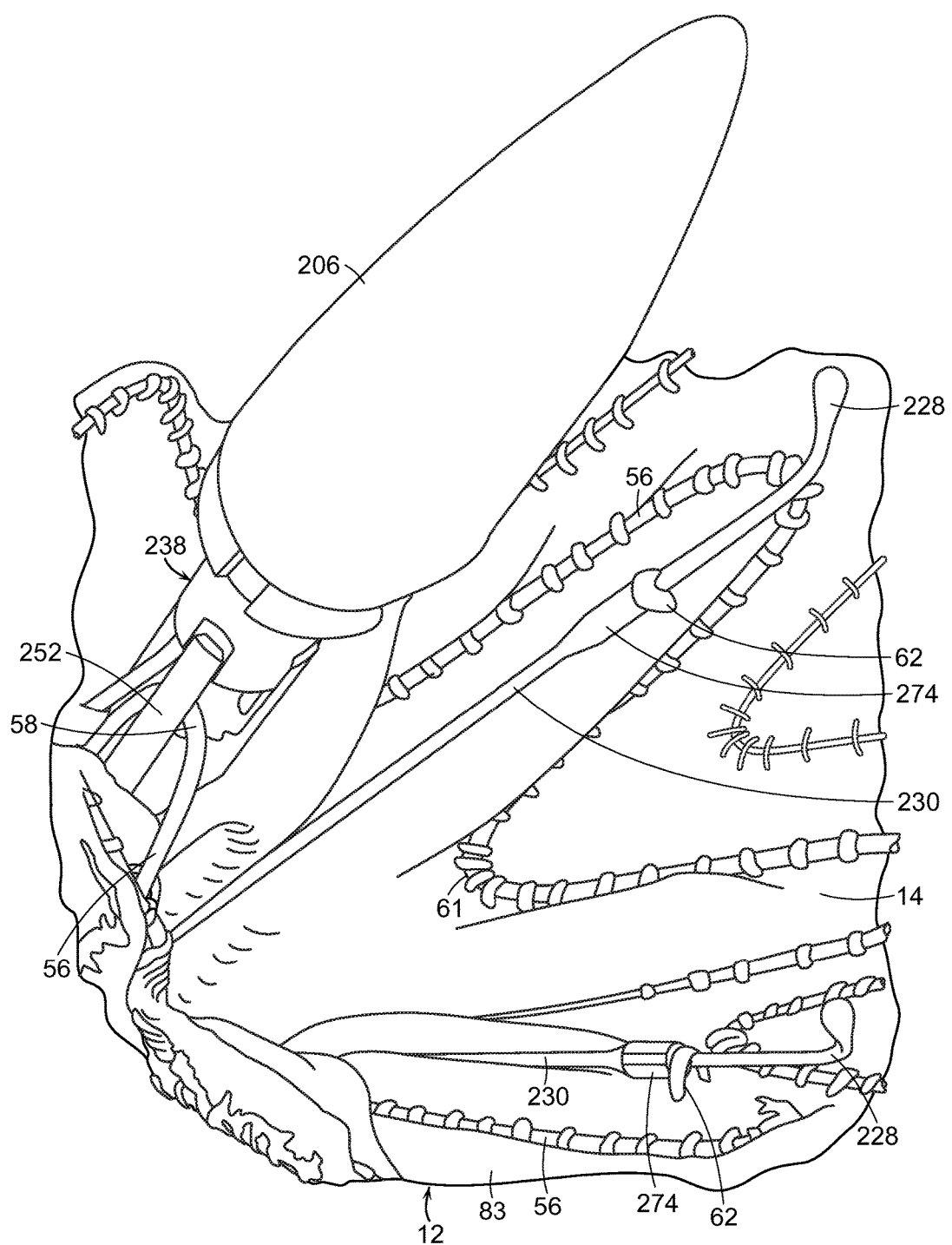
FIG. 11 is a perspective view of one embodiment of an aortic assembly system of the invention mounted on one embodiment of a delivery system of the invention.

In a specific embodiment, inferior portion 83 is on one side of tubular aortic component 12 opposite wall aperture 20 and is essentially parallel to major longitudinal axis 24 of tubular aortic component 12, shown in FIG. 1B. Exposed apices 58 of clasping stent 56, when collapsed will cause at least partial collapse of proximal end 14 of tubular aortic component 12 at clasping stent 56, as can be seen in FIG. 11. At least one of support wire sutures 62 are at inferior portion 83 within tubular aortic component 12. In a specific embodiment, support wire sutures 62 are at apices of clasping stent 56. Preferably, support wire sutures 62 are separated by at least one proximal apex of clasping stent.

Figure 4A:
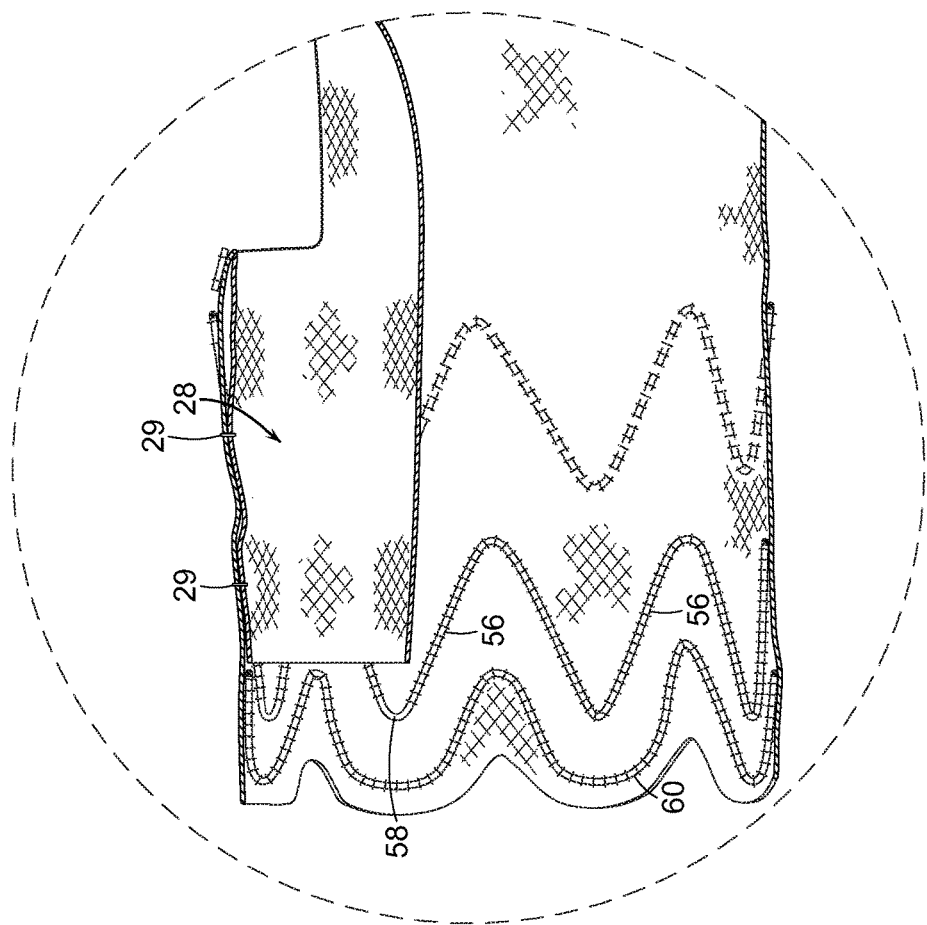
FIGS. 4A and 4B represent embodiments of an aortic assembly system of the invention, taken from views 4A and 4B of FIGS. 2A and 2B.
Figure 4B:
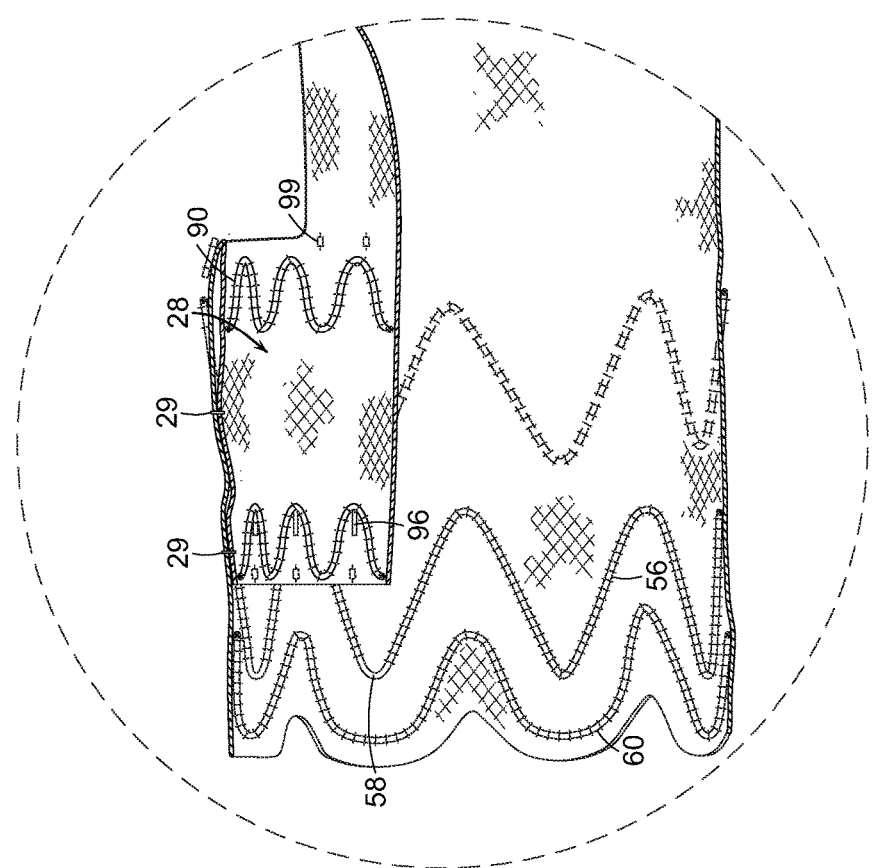

In one embodiment, distal end 32 of tunnel graft 28 has a diameter greater than that of proximal end 30 of tunnel graft 28, as can be seen in FIGS. 2A and 3A. In another embodiment, proximal end 30 of tunnel graft 28 is between the most proximal edge of proximal end 14 of tubular aortic component 12 and proximal end 22 of wall aperture 20, as shown in FIGS. 2A, 2B, 3A, 3B, 4A and 4B. As shown in FIGS. 4A and 4B, tunnel graft 28 is secured to an interior wall of tubular aortic component 12 by a suitable means, such as by sutures 29.

As can be seen in FIGS. 1B, 1C, 2A, 2B, 3A and 3B, tunnel graft 28 includes open portion 84 at wall aperture 20. Tubular portion 86 extends proximally from open portion 84, as shown in FIGS. 2A, 2B, 3A and 3B. In one embodiment, tubular portion includes stents 88, 90 at each of a proximal 92 and distal end 94 of tubular portion 86, as shown in FIGS. 2B and 3B. Preferably, stents 88, 90 at proximal 92 and distal 94 ends of tubular portion 86 includes proximal and distal apices connected by struts. Preferably, stent 88 at proximal end 92 of tubular portion 86 includes at least one barb 96 (FIG. 2B). In another embodiment shown in FIG. 3B, barbs 96 extend for distal apices of stent 98 of tubular portion 86. Optionally, tubular portion 86 further includes at least one stent 98 between stents 88, 90 at proximal 92 and distal 94 ends, respectively, of tubular portion 86. Preferably, at least one of stents 98 between stents 88, 90 at proximal end 92 and distal end 94 includes at least one barb. Most preferably, stents of tubular portion 86 include nitinol.

As can also be seen in FIGS. 2A and 2B and 3A and 3B, 4A and 4B, distal end 94 of tubular portion 86 is generally conical, whereby distal end 94 of tubular portion 86 essentially matches proximal end 92 of tunnel graft 28 at proximal end 22 of wall aperture 20, as a continuum or, optionally, at a seam, not shown. In one embodiment, a maximum diameter of proximal end of tunnel graft 28 is equal to or less than the diameter of distal end of tubular portion 94. Examples of suitable maximum diameters of proximal end 30 of tunnel graft 28 include, for example, diameters equal to or greater than a diameter selected from the group consisting of about 6 mm, about 8 mm, about 10 mm, about 12 mm or about 14 mm.

Preferably, tubular portion 86 has a major longitudinal axis that is parallel to major longitudinal axis 24 of tubular aortic component 12. Proximal end 92 of tubular portion 86 is distal to the most proximal edge of proximal end 14 of tubular aortic component 12. In one embodiment, not shown, proximal end 92 of tubular portion 86 is coterminous with the most proximal edge of proximal end 14 of tubular aortic component 12 or, alternatively, as shown in FIGS. 2A and 2B and 3A and 3B, 4A and 4B, is distal to proximal end 14 of tubular aortic component 12. In another embodiment, tubular portion 86 has a major axis at an angle A 81 relative to major longitudinal axis 24 of tubular aortic component 12, as shown in FIG. 9A. In one embodiment, the angle is in the range of at least one of between about 0° and about 90°, such as 10°, 20°, 30°, 45°, 60°, and 90° C.

Figure 9B:
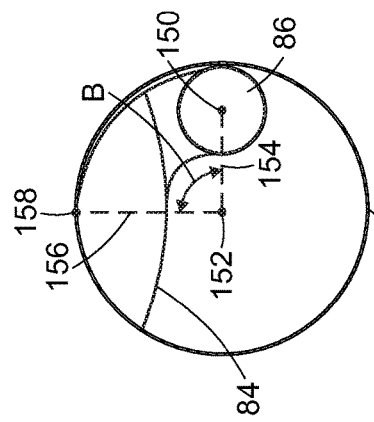
FIGS. 9B and 10B represent further embodiments of an aortic assembly system of the invention taken along lines 9B and 10B of FIGS. 10A and 10B, respectively.
Figure 9A:
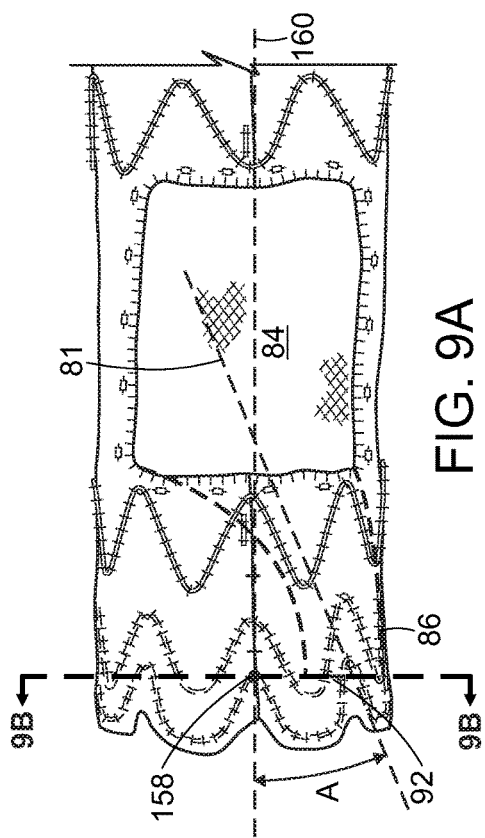
FIGS. 9A and 10A represent additional embodiments of an aortic assembly system of the invention.

Further, as shown in FIGS. 9A and 9B, proximal end 92 of tubular portion 86 has geometric center 150 that is distinct from a geometric center 152 of tubular aortic component 12, wherein line 154 defined by geometric center 150 of proximal end 92 of tubular portion 86 and geometric center 152 of tubular aortic component 12 in a plane defined by proximal end 92 of tubular portion 86, taken along line 9 B of FIG. 9A, is at a positive angle B from line 156 defined by geometric center 152 of tubular aortic component 12 and point 158 along centerline 160 bisecting wall aperture 20 and parallel to major longitudinal axis 24 (FIG. 1A) of tubular aortic component 12, point 158 being in the same plane as the geometric centers 150, 152 of proximal end 92 of tubular portion 86 and tubular aortic component 12, respectively. Examples of suitable positive angles B can be at least one member selected for the group consisting of ±10°, ±20°, ±30°, ±45°, ±60°, ±90°, ±120°, ±135°, ±160°, ±170° and 180°.

Figure 10B:
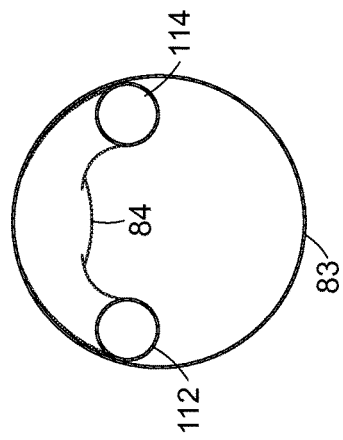
Figure 10A:
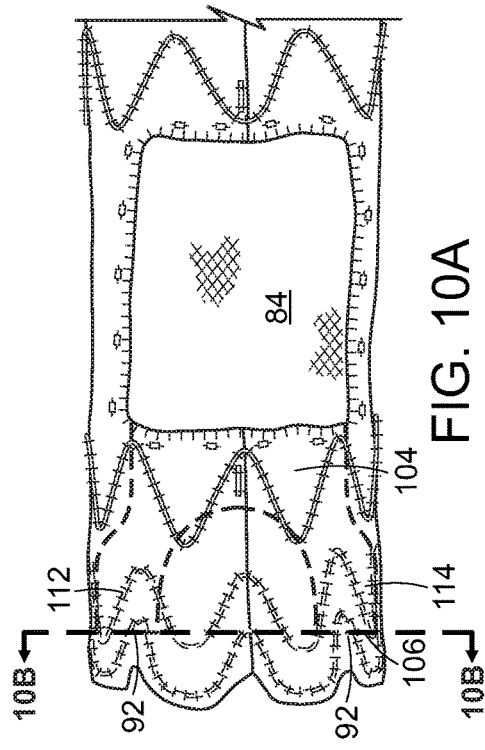

In one embodiment, at least one radiopaque marker 99 is located at at least one of proximal end 92 of tunnel graft 28 and distal end 94 of tubular portion 86 of tunnel graft 28, as shown in FIGS. 2B, 3B and 4B. Another embodiment includes tubular portion 100 and further includes second tubular portion 102 of tunnel graft 28 extending proximal to open portion 84 of the tunnel graft 28, wherein second tubular portion 102 has distal end 104 and proximal end 106 as shown in FIGS. 7A, 7B, 8A and 8B. In one embodiment, not shown, second tubular portion 102 is of unequal length to that of first tubular portion 100. In another embodiment, shown in FIGS. 7A and 7B, second tubular portion 102 is parallel to first tubular portion 100. First tubular portion 100 and second tubular portion 102 are each a distinct, and integrally complete tubular portion. In another embodiment, shown in FIGS. 8A and 8B, tubular portions share common wall of a first graft material 108 that partition a conduit of the second graft material 110. In this embodiment, first 108 and second 110 graft materials define, at least in part, first tubular portion 100 and second tubular portion 102. As shown in FIGS. 10A and 10B, tubular portions 112 and 114 extend away from each other and proximally from open portion 84.

In still another embodiment, shown in FIGS. 2A, 2B, 3A, 3B, 4A and 4B, proximal end 92 of tunnel graft 28 has a diameter in a range between about 5 mm and about 10 mm, or between about 5 mm and about 15 mm, or between about 8 mm and about 15 mm. Generally, tubular portion 86 has a length in a range of between about 20 mm and about 60 mm, or between about 20 mm and about 100 mm. Most commonly, tubular portion 86 has a length in a range between about 30 and 50 mm. Preferably, proximal end 92 of tunnel graft 28 is within at least about 5 mm, about 10 mm, and about 15 mm or about 20 mm of proximal end 14 of tubular aortic component 12.

Figure 12:
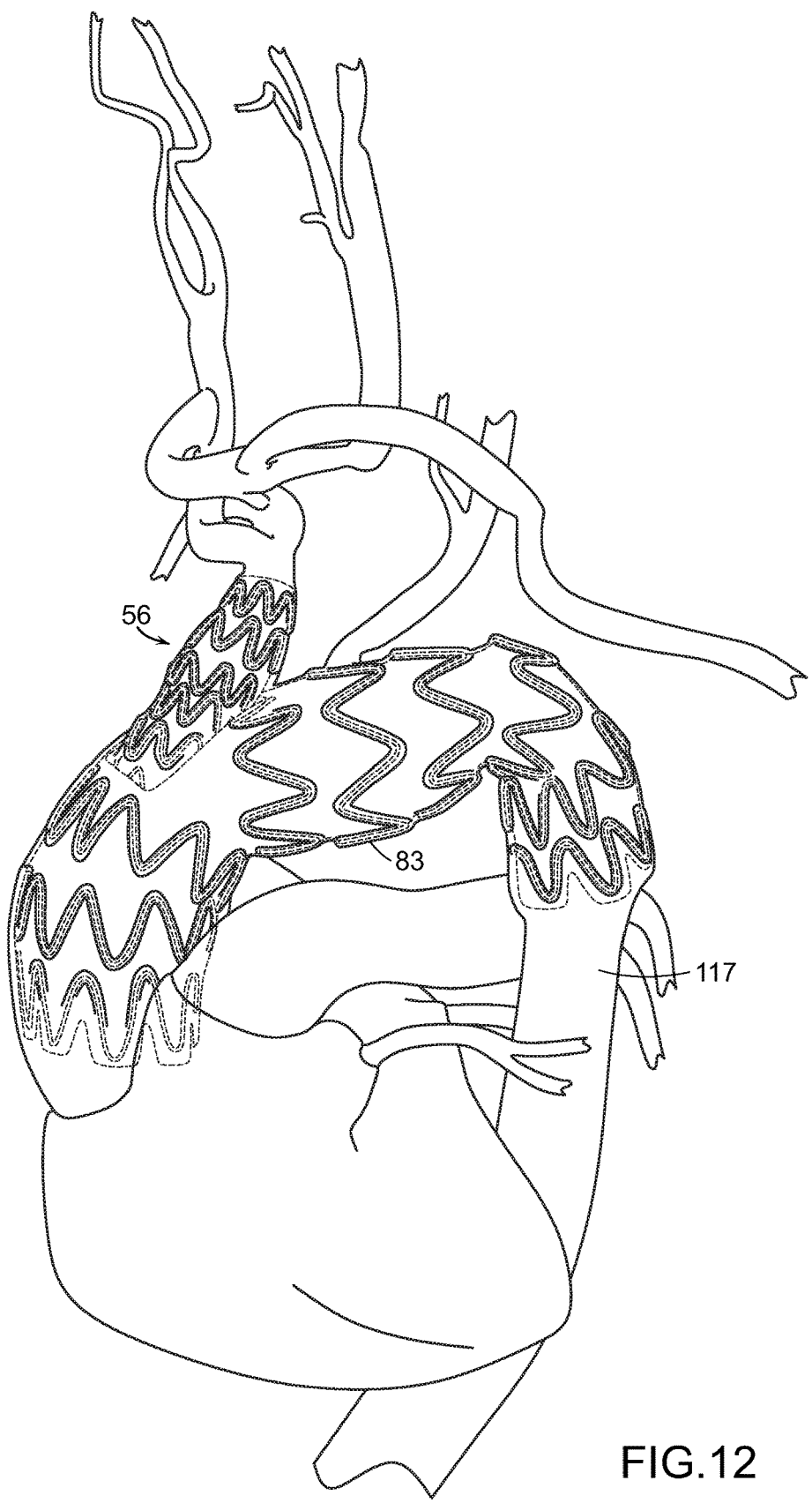
FIG. 12 represents placement of an embodiment of an aortic graft assembly of the invention in the ascending aorta, aortic arch and a portion of the descending aorta of a subject.
Figure 13:
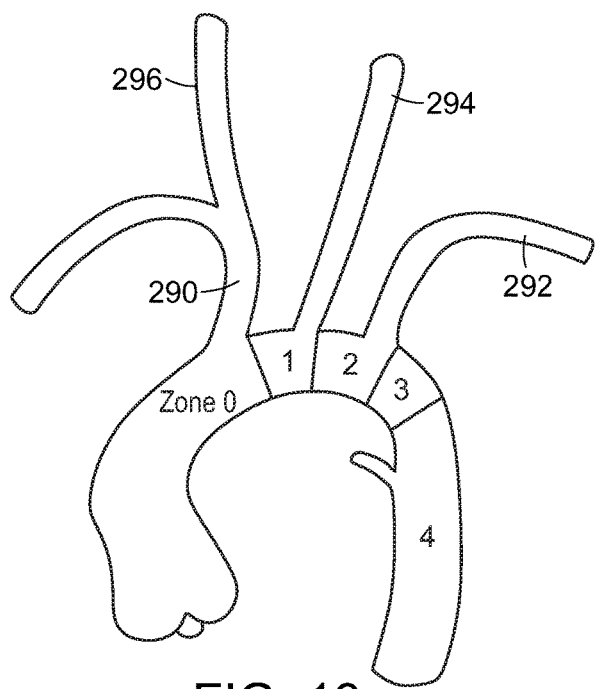
FIG. 13 represents zones (0, 1, 2, 3 and 4) of the aorta and major vessels branching from the aorta (prior art).
Figure 14:
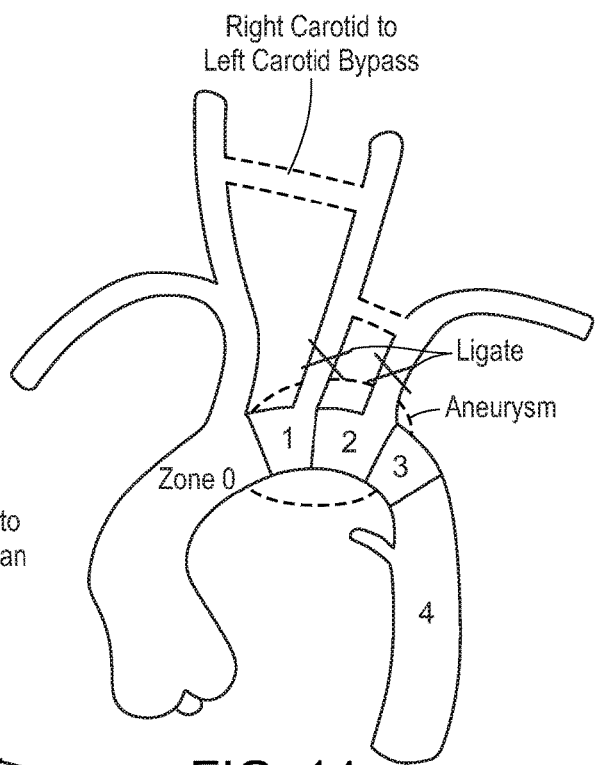
FIG. 14 represents zones (0, 1, 2, 3 and 4) of the aorta, an aortic aneurysm, a right carotid artery to left carotid artery bypass, a left carotid artery to left subclavian artery bypass and ligation of the left carotid and left subclavian arteries (prior art).
Figure 15:
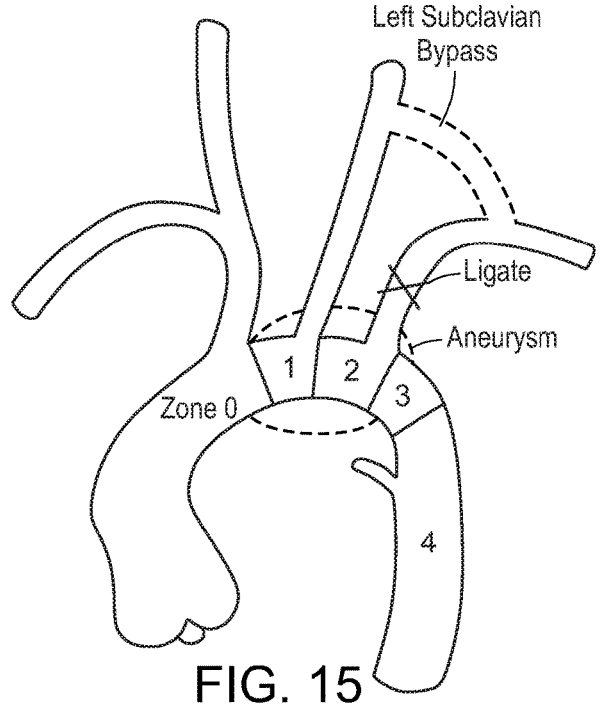
FIG. 15 represents zones (0, 1, 2, 3 and 4) of the aorta, an aortic aneurysm, a left carotid artery to left subclavian artery bypass and ligation of the left subclavian artery (prior art).

FIG. 12 shows one embodiment of aortic graft assembly 10 of the invention fully deployed within aorta 117 of a patient. FIGS. 13-15 show various stages of an aortic bypass operation (prior art).

As shown, in FIGS. 16A-16F, aortic graft assembly 200 (FIG. 16A) includes delivery component 202 (FIG. 16B) to which tubular aortic component 12 (FIG. 16A) is attached (FIGS. 16A and 16C). Delivery component 202 includes control catheter 204 (FIG. 16B), about which tubular aortic component 12 (FIG. 16C) extends, nose cone 206 (FIGS. 16B and 16C) is fixed at a distal end of control catheter 204 (FIGS. 17A and 17B).

Figure 17A:
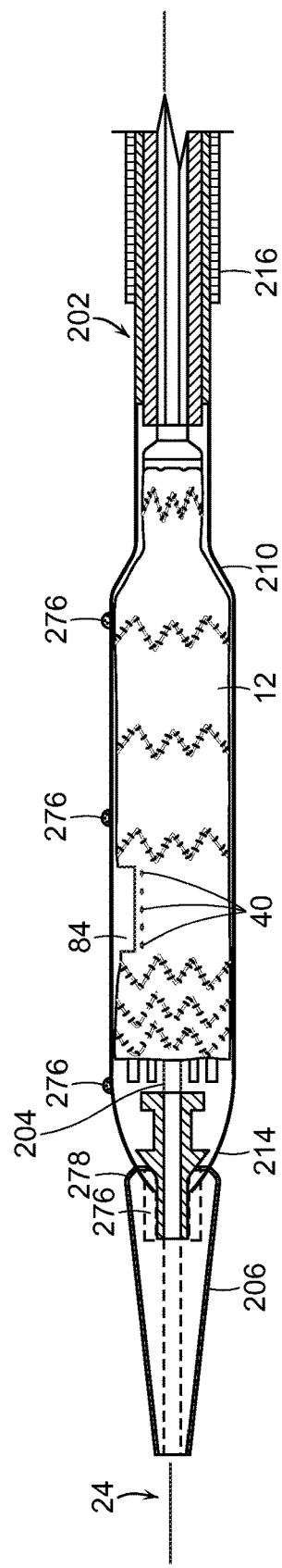
Figure 17B:
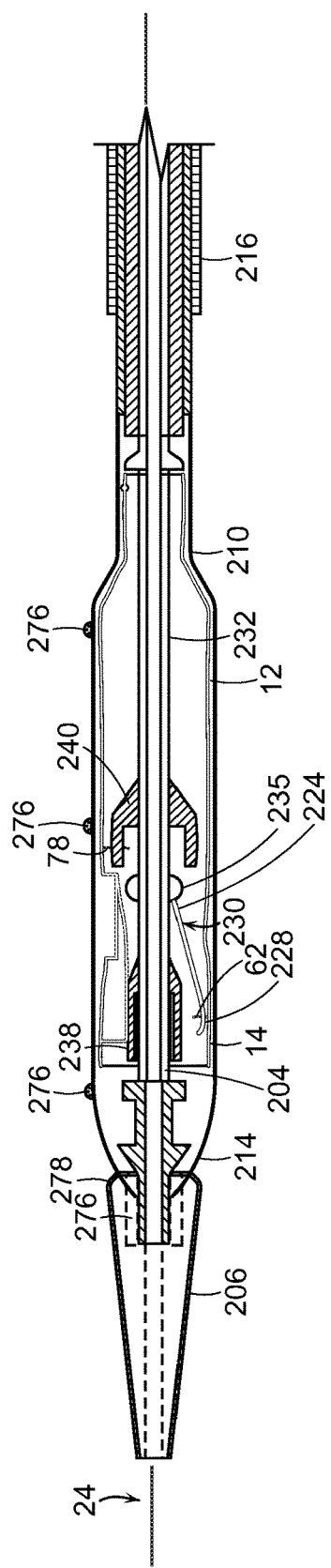
Figure 18:
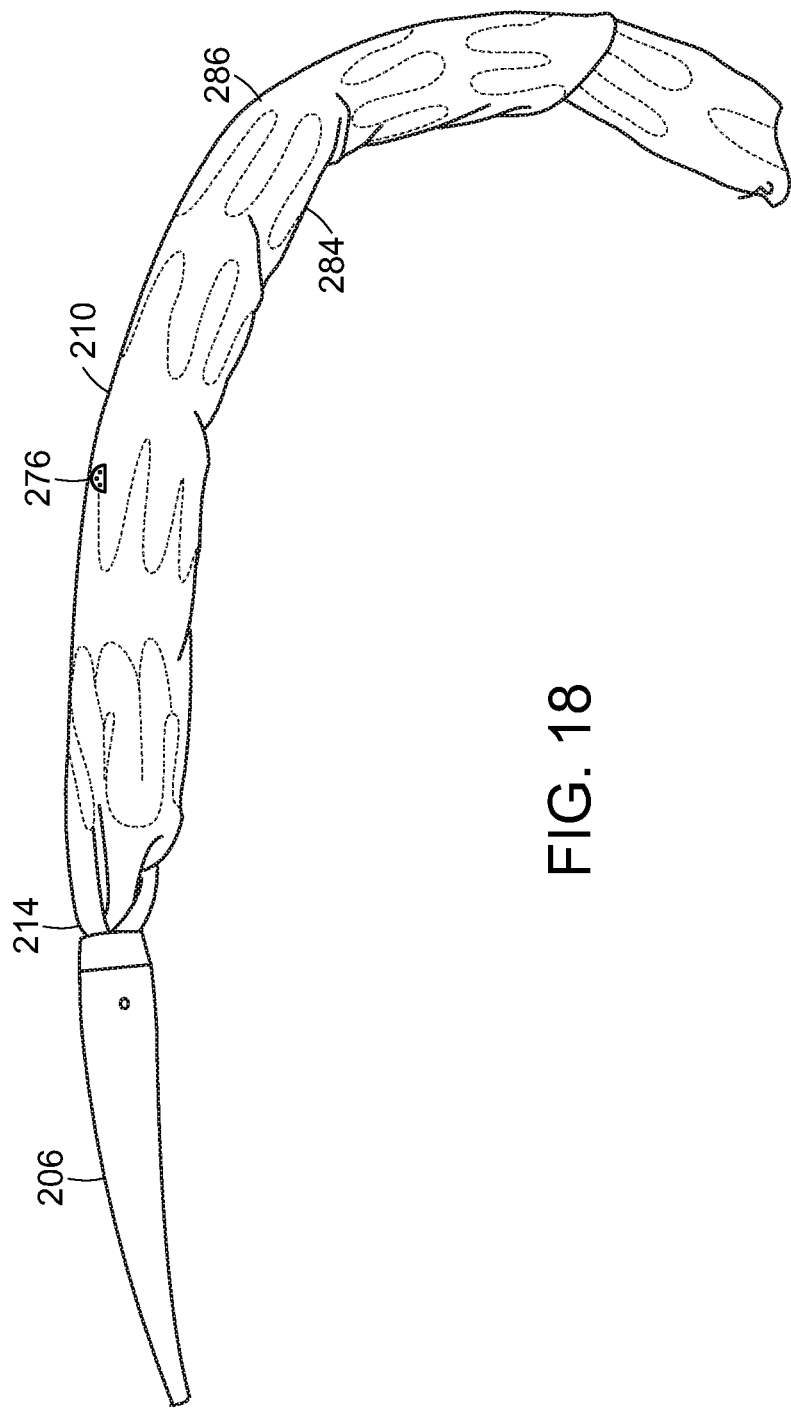
FIG. 18 is a perspective view of a nose cone, and inner sheath tucked into a proximal cavity of the nose cone of one embodiment of the invention.
Figure 20:
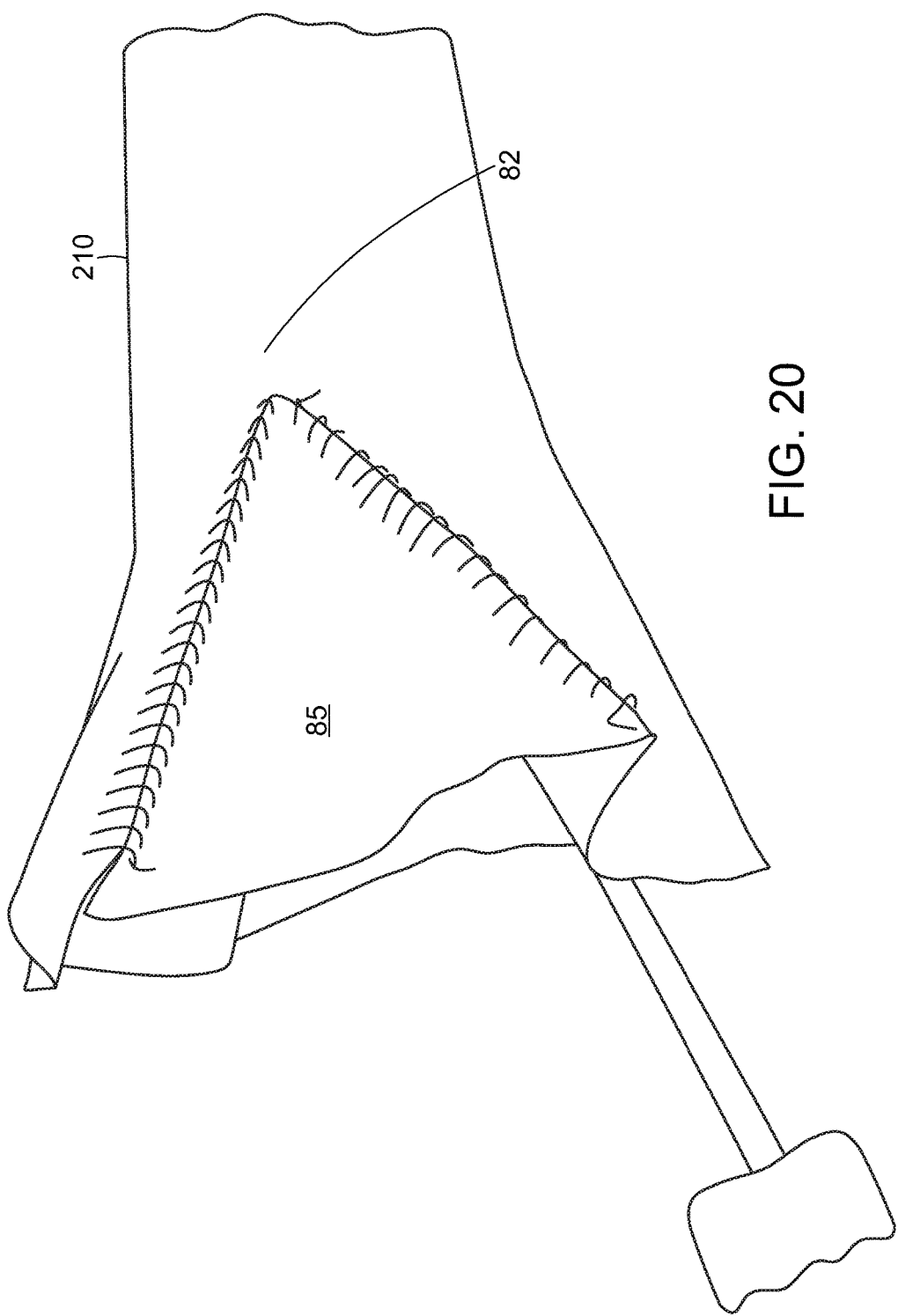
FIG. 20 represents an alternative embodiment of an inner sheath of an embodiment of a delivery system of the invention.
Figures 25A, 25B:
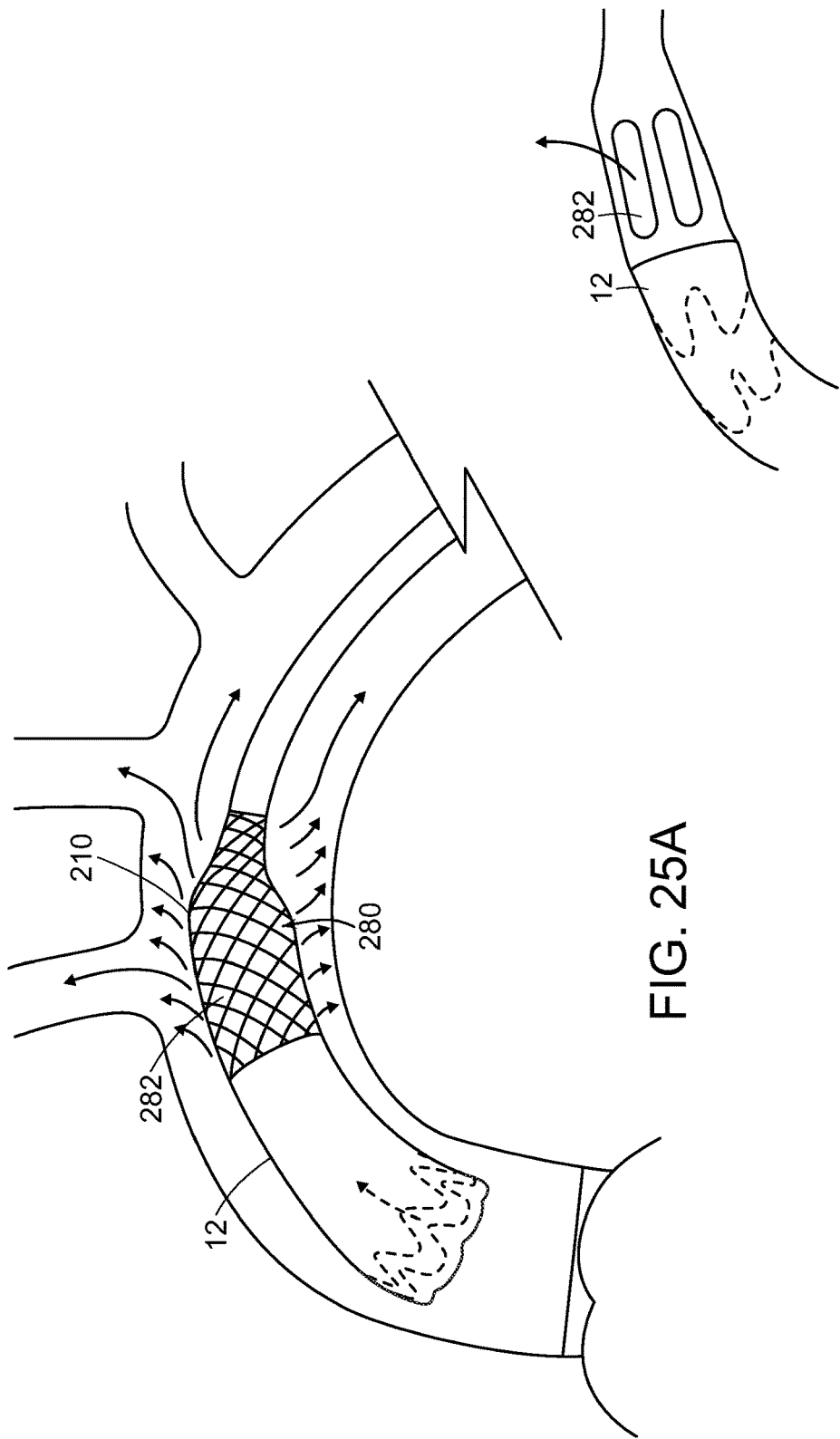
FIGS. 25A and 25B represent alternative embodiments of an inner sheath component of one embodiment of the invention.

In one embodiment, shown in FIGS. 17A, 17B and 17C, delivery component 202 further includes inner sheath 210 extending about control catheter 204. A distal opening at distal end 214 of inner sheath 210, can be tucked into nose cone 206 (FIGS. 17A, 17B and 18). In still another embodiment, shown in FIGS. 19A and 19B, inner sheath 210 includes inferior portion 82, said inferior portion 82 having fluted portion 85 as can be seen in FIG. 20. Optionally, as can be seen in FIGS. 21A and 21B, inner sheath 210 can be tapered to narrow toward distal end 211 or of essentially constant diameter. In one embodiment, inner sheath 210 defines at least one through hole 280 at proximal end 282 of inner sheath 210, as shown in FIGS. 25A and 25B.

As can be seen in FIGS. 17A and 17B, introducer sheath 216 extends about inner sheath 210 and about tubular aortic component 12, wherein introducer sheath 216 is retractable relative to inner sheath 210 to thereby release distal end 214 of inner sheath 210. Nose cone 206 can thereafter be retracted within inner sheath 210.

Figure 22:
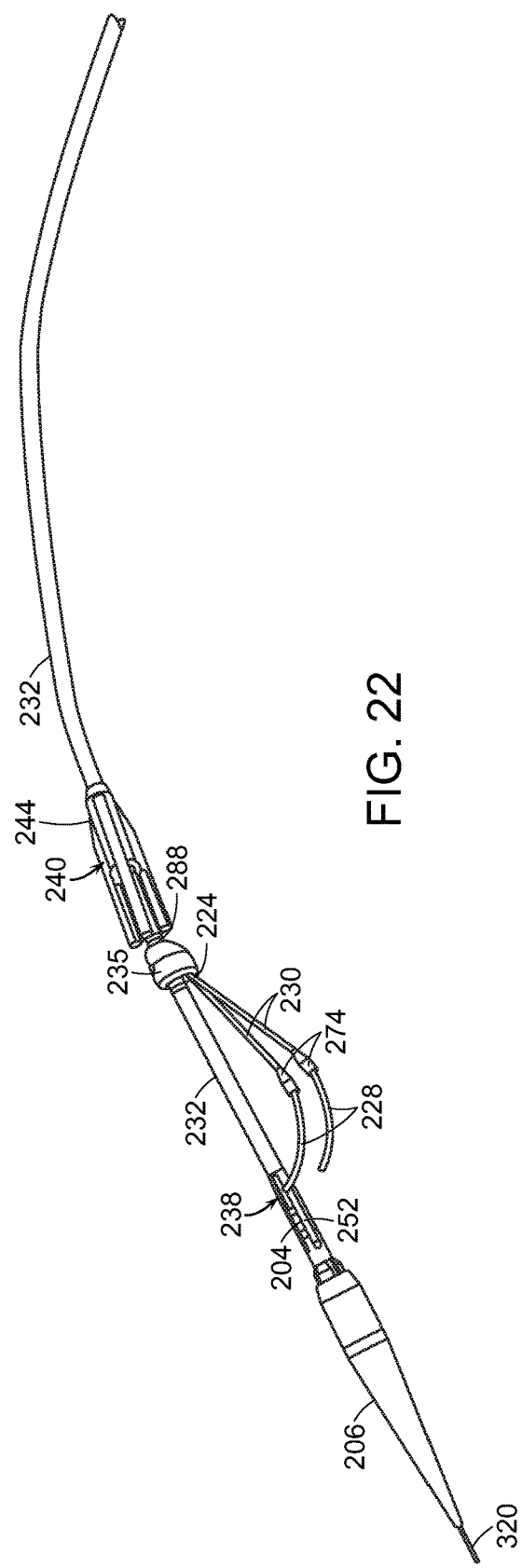
FIG. 22 represents an embodiment of a portion of a delivery system employed by the invention.
Figure 23A:
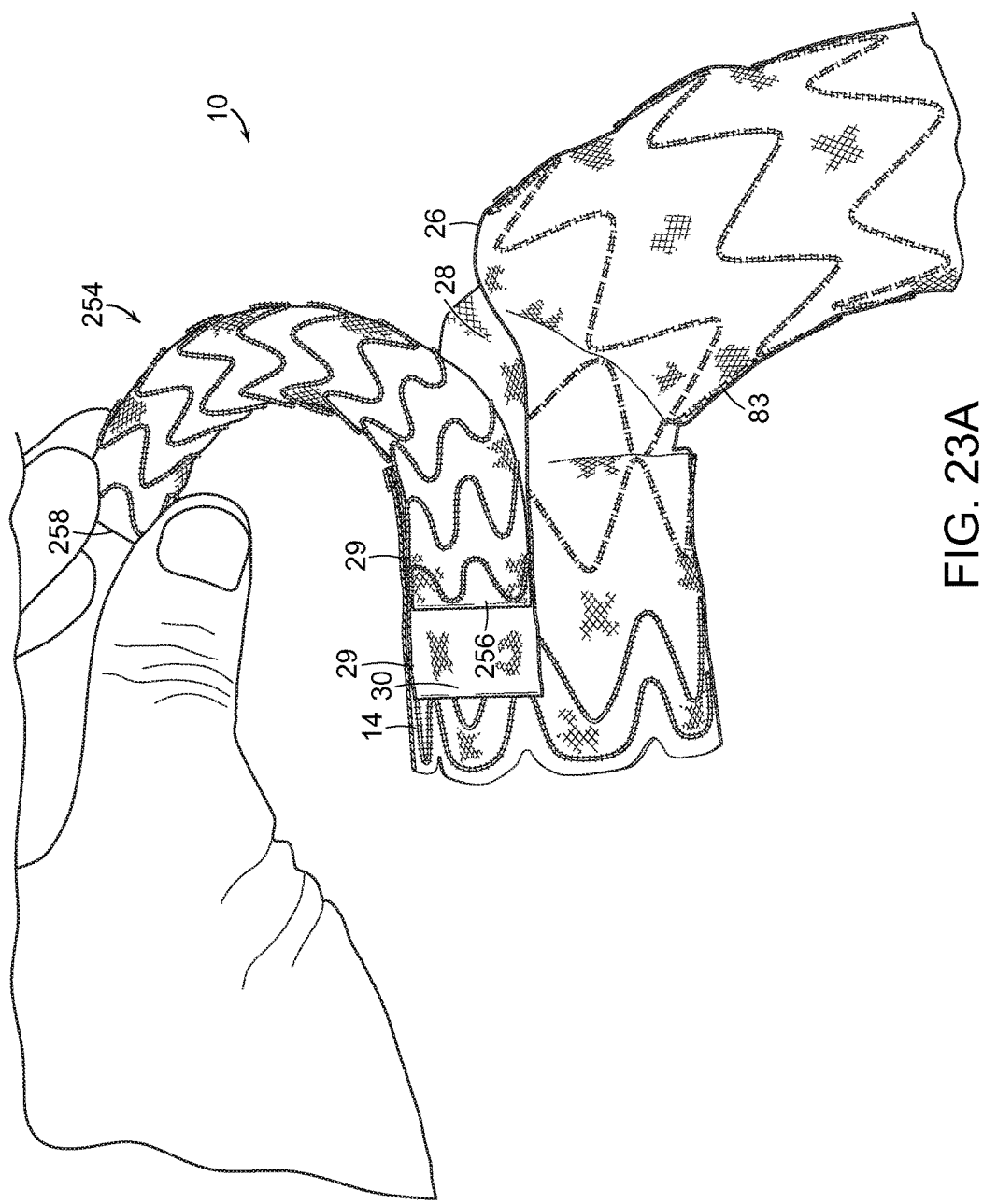
FIGS. 23A-23D represent additional views of an aortic assembly system and branch graft of the invention.
Figure 23B:
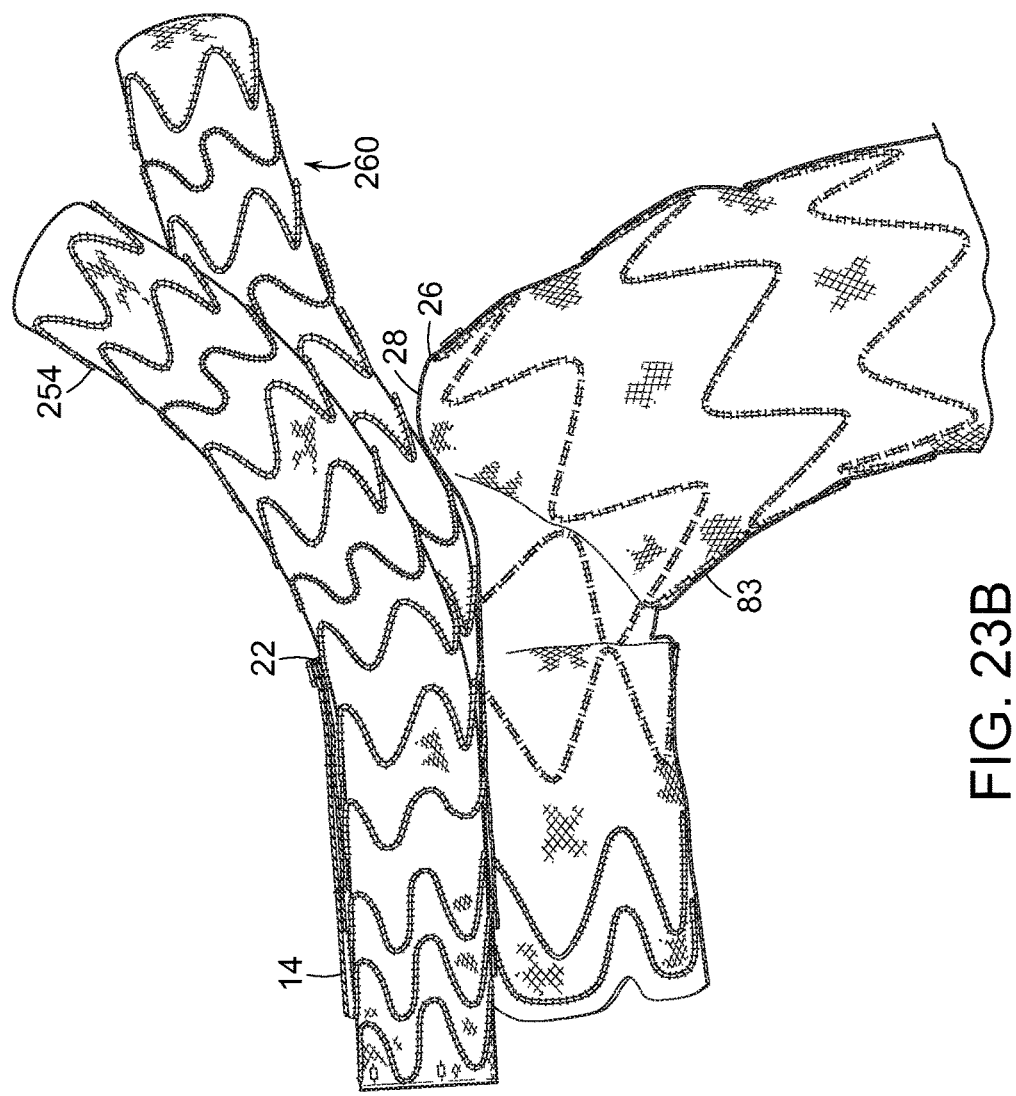
Figure 23C:
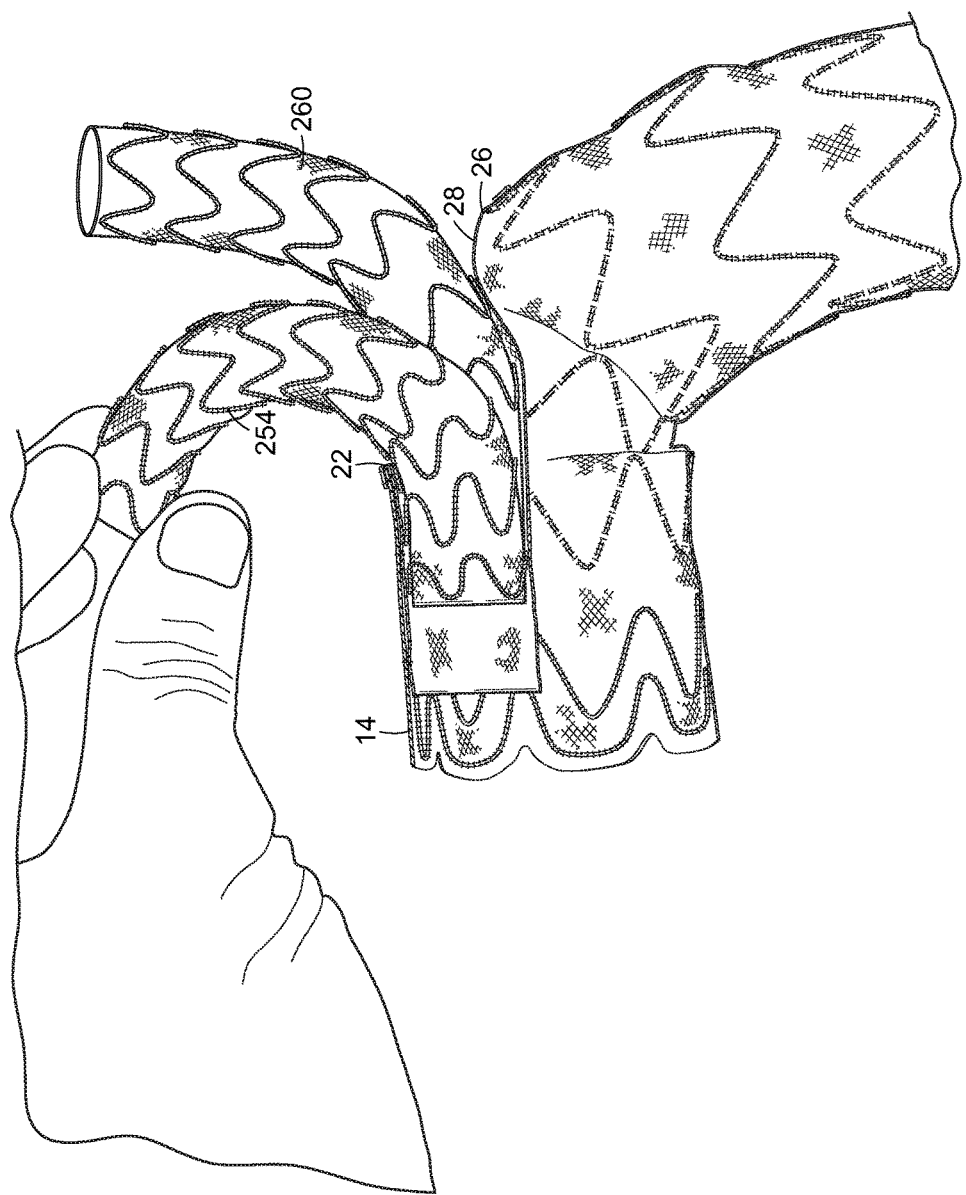
Figure 23D:
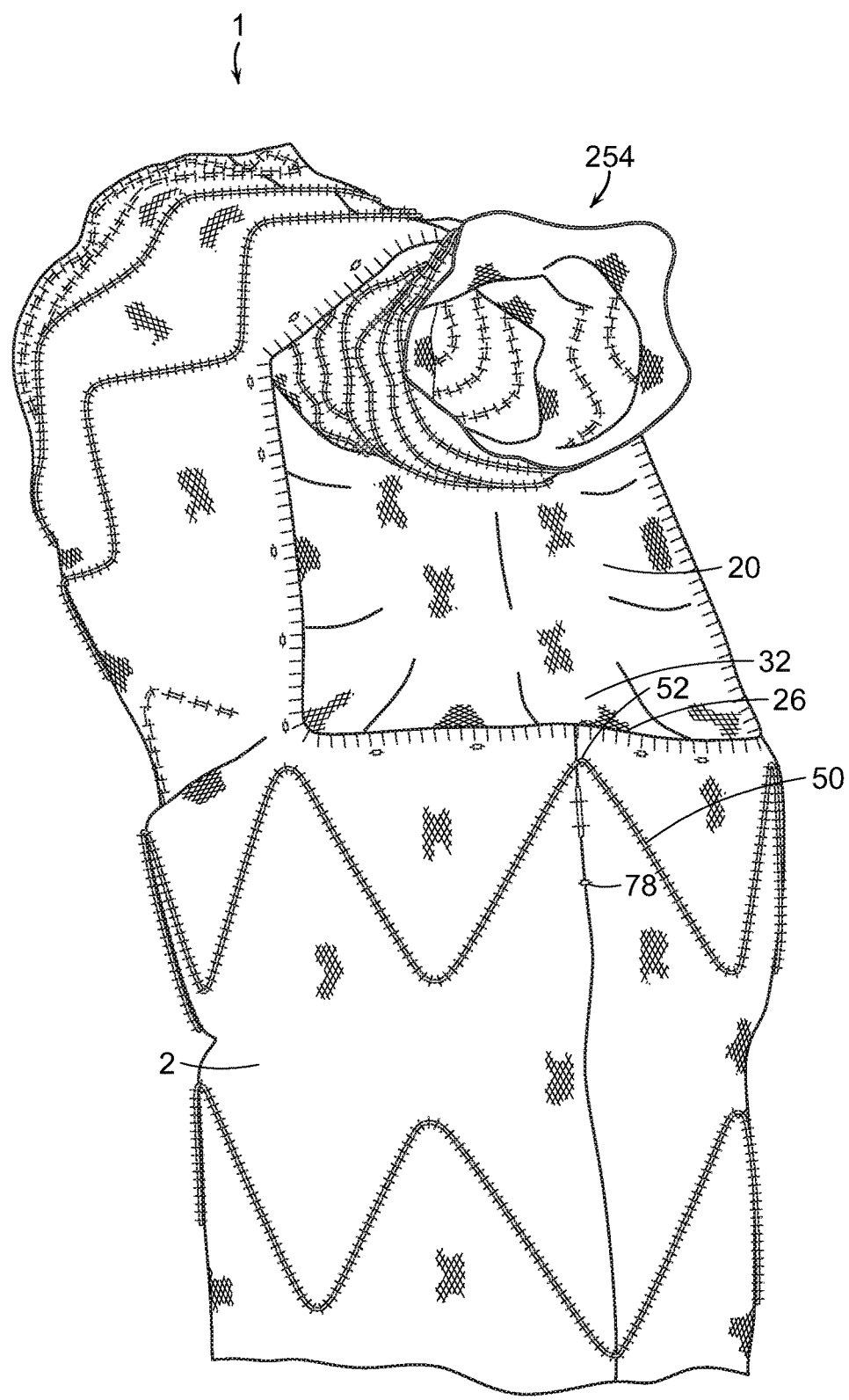

Delivery component 202, shown in FIGS. 17A, 17B, 17C and 22, further includes at least one supporting wire 230 fixed at proximal end 224 to support base 235, substantially parallel to a major longitudinal axis of outer control tube 232 and free at the distal end 228, wherein free end 228 of at least one of supporting wire 230 and internal sutures 62 (FIG. 17B) at the proximal end 14 of tubular aortic component 12 releasably secures proximal end 14 of tubular aortic component 12 to at least one of supporting wires 230. Outer control tube 232 is slidable along control catheter 204. Supporting wires 230 are fixed at proximal ends 224 to support base 235 at outer control tube 232 distal to proximal apex clasp 240. Free ends 228 of support wires 230 are proximate to proximal end 14 and to nose cone 206. Proximal portion 252 of distal apex clasp 238 and outer control tube 232 are slidable along the control catheter 204 with movement of outer control tube 232 (FIGS. 16B and 22). Distal apex clasp 238 fixes proximal end 14 of tubular aortic component 12 by securing exposed apices 58 (FIG. 16C) of clasping stent 56 at proximal end 14 of tubular aortic component 12. As shown in FIG. 16B, distal portion 248 of distal apex clasp 238 mates with of teeth 252 of proximal portion 250 of distal apex clasp 238 in a closed position that secures exposed apices 58 of clasping stent 56 of tubular aortic component 12.

Proximal apex clasp 240 is at outer control tube 232 (FIG. 17B). Proximal apex clasp 240 includes teeth 246 (FIG. 16B) extending distally from proximal portion 244 of proximal clasp 240. Teeth 246 extend distally through retention component 78 of tubular aortic component 12, as shown in FIG. 17B.

As shown in FIGS. 23A-23D, tubular branch component 254 includes proximal end 256 and distal end 258, wherein proximal end 256 of tubular branch component 254 is configured to engage proximal end 30 of tunnel graft 28. In an embodiment, the engagement is by interfering relation between tubular branch component 254 and tunnel graft 28. When aortic graft assembly 10 is implanted in the aorta of a patient, a seal forms with at least one member of the group consisting of the proximal end of at least one of the tubular aortic component 12, tubular branch component 254 and second tubular branch component 260, and the distal end of at least one of tubular aortic component 12, tubular branch component 254 and second tubular component 260. A "seal"

as defined herein, means that essentially no fluid will seep between the wall of a first conduit and the wall of a second conduit within which the first conduit is located. Such seals typically will be at the most proximal portion of a juncture between nested first and second conduits.

In one embodiment, supporting wire 230 has at least one stop 274 (FIG. 11), wherein stop 274 limits movement of suture loop 62 along supporting wire 230.

In another embodiment, tubular aortic component 12 includes radiopaque sutures 18 and inner sheath 210 includes radiopaque markers 276, all of which are longitudinally aligned along a path of relative movement of inner sheath 210 (FIGS. 16A-16F and 17A-17C) and tubular aortic component 12 during deployment of tubular aortic component 12, and are spaced apart from each other, whereby partial retraction of inner sheath 210 will cause overlap of radiopaque markers 276 with radiopaque markers 38. In one embodiment, radiopaque markers 38 are also, or alternatively, on superior portions of inner sheath 210 and tubular aortic component 12. Preferably, radiopaque markers 38, 276 are asymmetric, wherein a shape of radiopaque markers 38, 276 changes as radiopaque markers 38, 276 are aligned with a surgical site. Preferably, radiopaque markers 38, 276 of tubular aortic component 12 are elongated and are substantially aligned with the major longitudinal axis 24 of inner sheath 210.

In a preferred embodiment, referring back to FIGS. 16A-16F and 17A-17C, tubular aortic component 12 is further constrained at at least one end by a clasp, such as distal apex clasp 238 or proximal apex clasp 240, and the method includes the step of releasing the clasp with retraction of supporting wire 230 from suture loop 62 of tubular aortic component 12. In this embodiment, preferably, tubular aortic component 12 further includes at least one radiopaque marker 38, wherein, preferably, radiopaque marker 38 is located on tubular aortic component 12 facing away from cavity 284 (FIG. 18) of the curve 286 (FIG. 18) defined by control catheter 204. Preferably, inner sheath 210 further includes at least one radiopaque marker 276, wherein radiopaque marker 276 of inner sheath 210 overlaps at least one radiopaque marker 276 of tubular aortic component 12 when tubular aortic component 12 is partially deployed. In still another embodiment, tubular aortic component 12 is further constrained by proximal clasp 240 and proximal fixed end 234 of supporting wire 230.

A method for implanting a prosthesis of the invention includes the steps of delivering tubular aortic component 12 within introducer sheath 216 along guidewire 320 through an aorta 262 to aneurysm 270 of the patient, shown in FIGS. 24A-24E. Tubular aortic component 12 is radially constrained and supported at least in part by control catheter 204 (FIGS. 16B, 16C, 16D), which is slidable along guidewire 320 (FIGS. 24A-24E). As shown in FIGS. 16A-16F and 17A-17C, tubular aortic component 12 is further longitudinally constrained by at least one supporting wire 230 extending from support base 235 at outer control tube 232 extending about and slidable along control catheter 204. Free end 228 of at least one of supporting wire 230 is arcuate and extends through suture loop 62 (FIG. 17B), within proximal end 14 of tubular aortic component 12.

Referring back to FIGS. 24A-24E, tubular aortic component 12 is guided to aneurysm 270 along guidewire 320. Inner sheath 210 (FIG. 17B), is partially retracted from tubular aortic component 12, whereby supporting wire 230 at least partially restricts longitudinal movement of proximal end 14 of tubular aortic component 12 until proximal end 14 of tubular aortic component 12 is secure within aorta 262 (FIGS. 24A-24E) of the patient to thereby prevent collapse of proximal end 14 of tubular aortic component 12 at an inferior portion 264 of aorta 262.

In one embodiment, inner sheath 210 is releasably secured at distal end 214 within a cavity defined by the proximal end of nose cone 206 (FIG. 18). In this embodiment, as shown in FIGS. 24A-24E, optional inner sheath 210 is partially retracted to release the distal end of the inner sheath 210 from nose cone 206 and thereby cause partial expansion of tubular aortic component 12. Wall aperture 20 is aligned over at least one vessel ostium 290, 292, 294 at aneurysm site 263 of the patient. Optionally, in embodiments of the invention that employ inner sheath 210, inner sheath 210 is then partially retracted to expose the proximal end 14 of tubular aortic component 12, including crown stent 56 and the clasping stent 60 (FIG. 1A). Control tube 232 is then partially extended to release bare apices 58 (FIG. 1A) of clasping stent 56 from distal clasp 238 and to release retention component 78 from proximal clasp 240 (FIGS. 16B and 17B), while retaining suture loops 62 on ends 228 of support wires 230 (FIGS. 16A-16F and 17A-17C). Nose cone 206 is then partially retracted into proximal end of tubular aortic component 12 and the delivery assembly and tubular aortic component 12 are then advanced to a final position within aorta 262 spanning aneurysm 263 of the patient. Control tube 232 is then further retracted to release suture loops 62 from ends 228 of support wires 230. Inner sheath 210 is then fully retracted (in embodiments of the invention that employ inner sheath 210) and then nose cone 206 and supporting wires 230 are fully retracted to complete deployment of tubular aortic component 12.

Figure 24B:
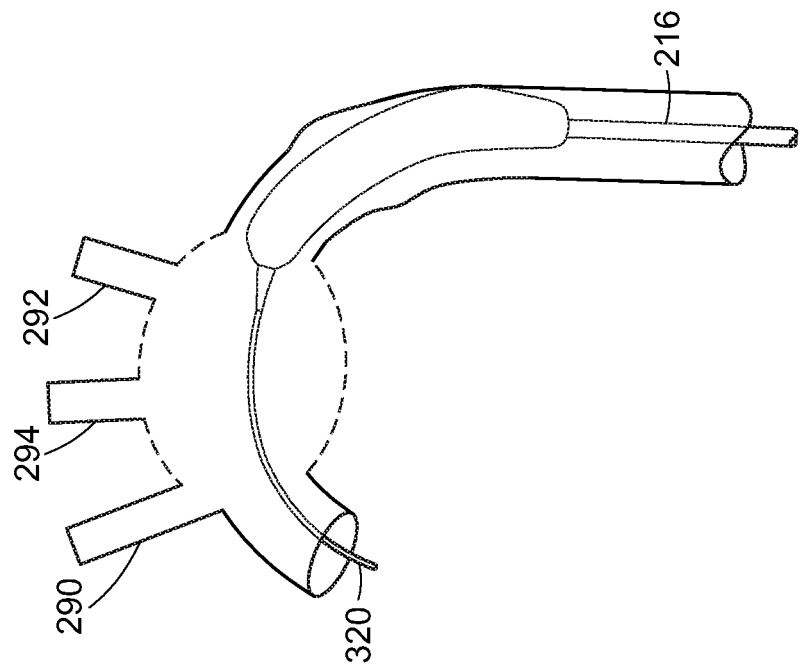
FIGS. 24A-24E represent method steps of one embodiment of a method of the invention.
Figure 24A:
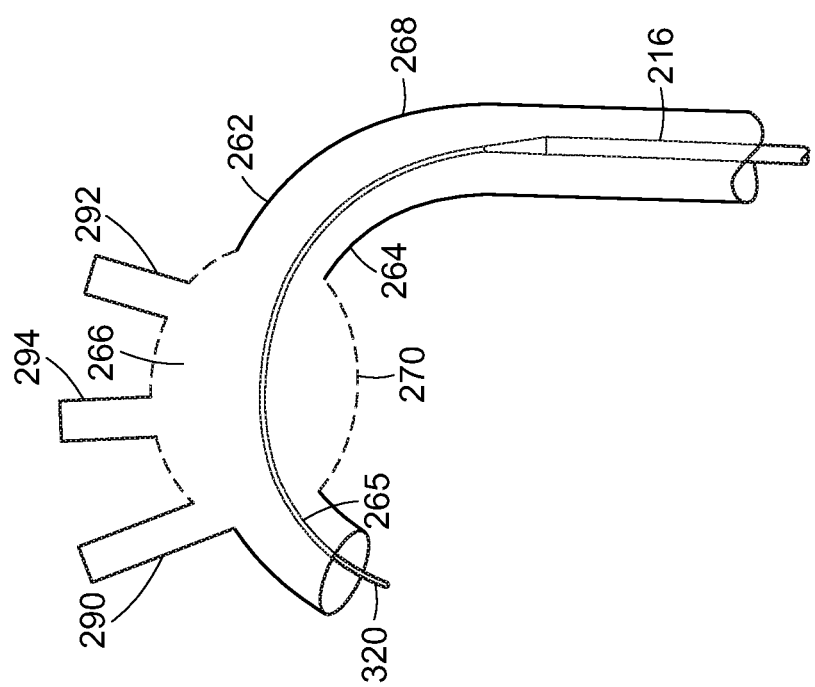
Figure 24C:
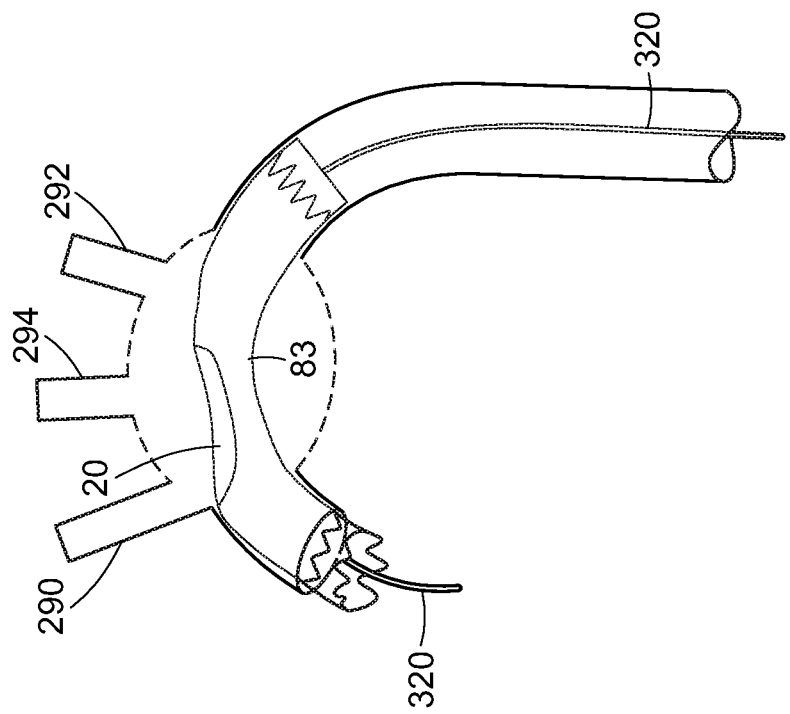
Figure 24D:
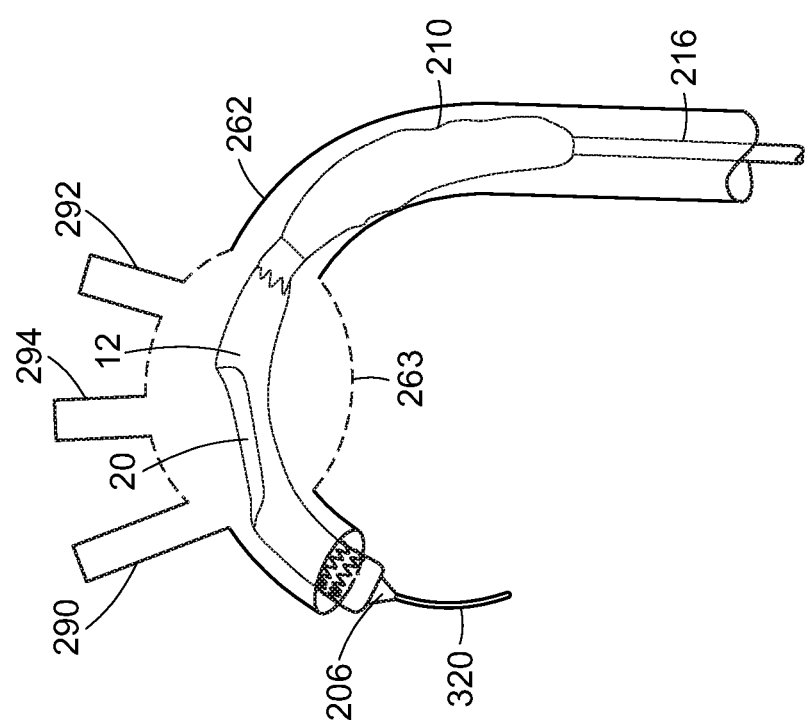
Figure 24E:
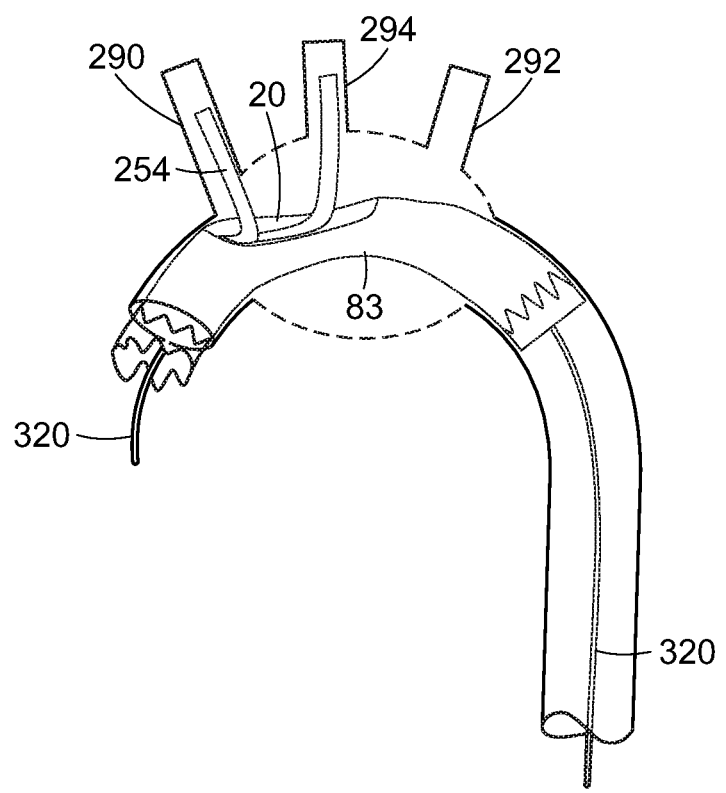

In an embodiment, the method of the invention includes the step of implanting at least one tubular branch component 254 in at least one of an innominate artery (also referred to as "brachiocephalic artery") 290, a left subclavian artery 292, a left common carotid artery 294, or right common carotid artery 296 of the patient into wall aperture 20 and tunnel graft 28 within tubular aortic component 12, as shown, with respect to the prior art, in FIGS. 13-15, and in FIGS. 24A-24E. In a preferred embodiment, the method of the invention includes the steps of implanting tubular branch component 254 into innominate artery 290, and another tubular branch component, into the left common carotid artery 294 (FIG. 24E).

Figure 26A:
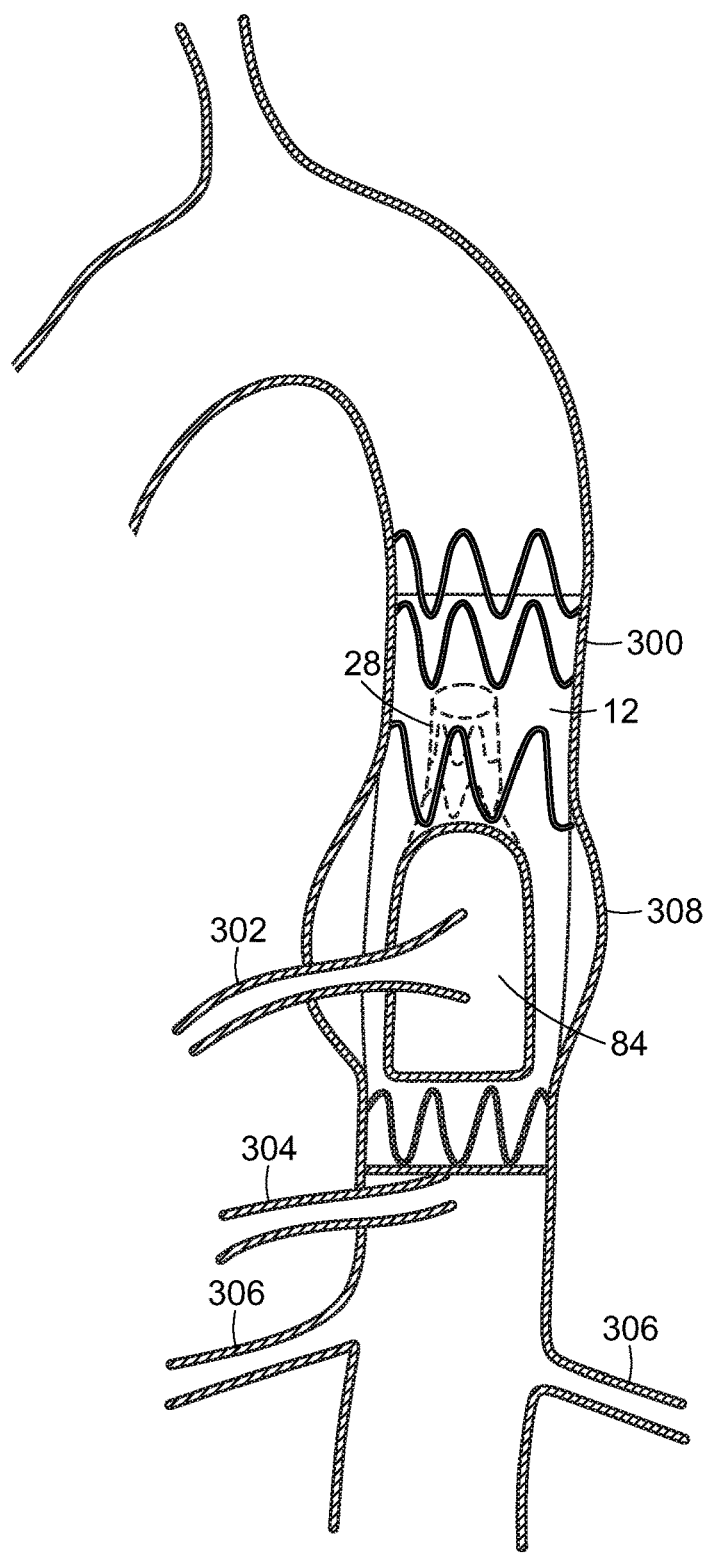
FIGS. 26A-26C represent method steps of one embodiment of an alternative method of the invention.
Figure 26B:
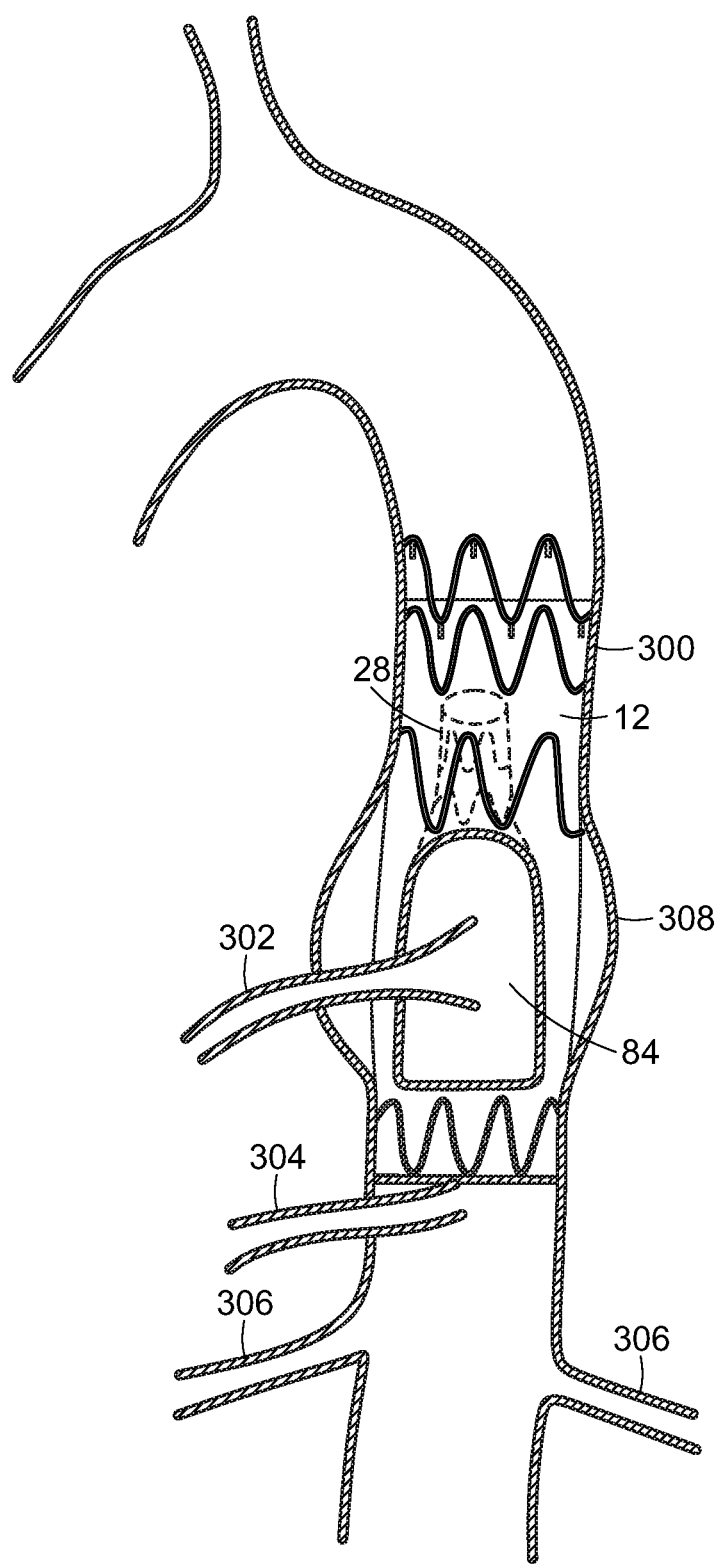
Figure 26C:
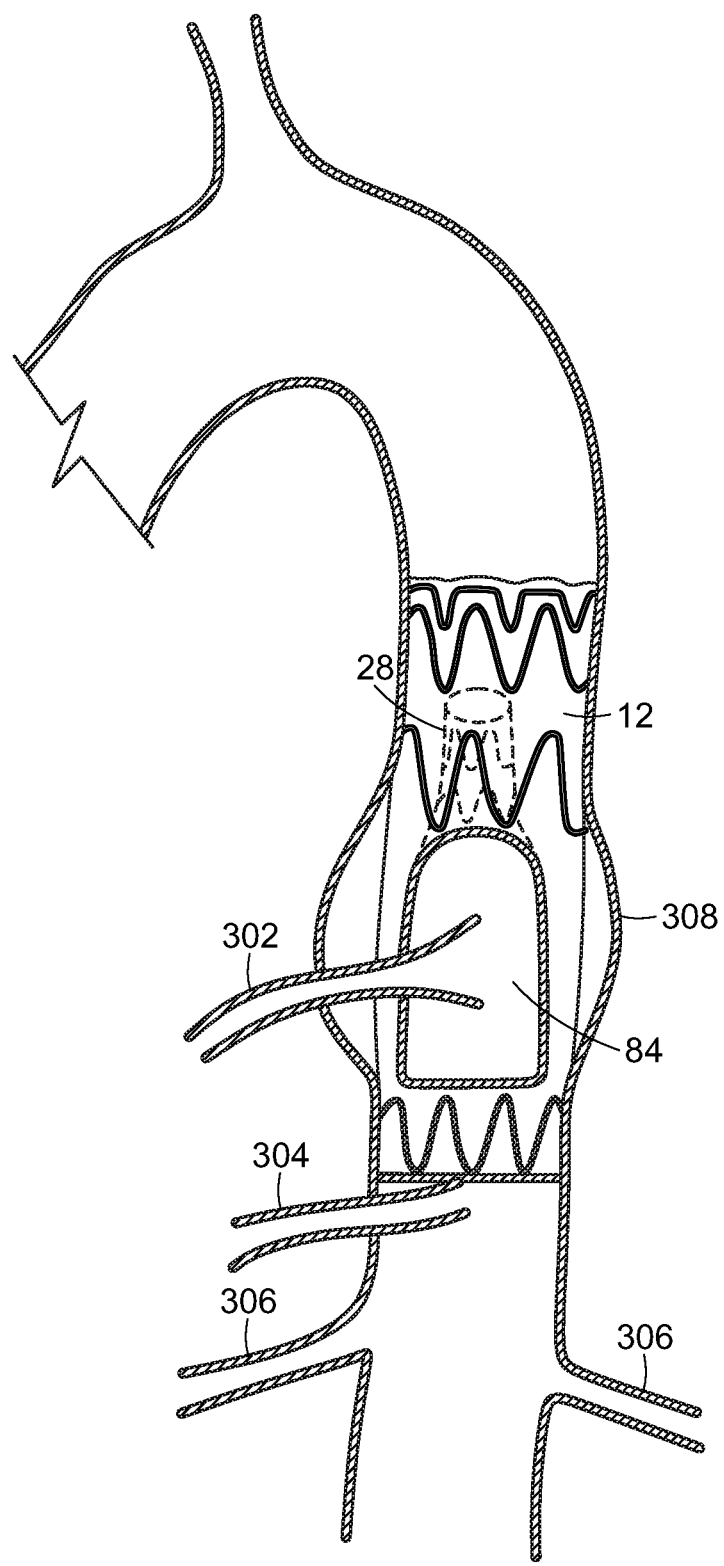

Implantation of the aortic graft assemblies of the invention can include implantation in at least one of a portion of the ascending aorta, the aortic arch, the descending aorta and abdominal aorta (see FIGS. 12, 24A-24E and 26A-26C). Implantation near, around or at the arch of the aorta, can include a right common carotid to left common carotid artery bypass with ligation of the left common carotid inferior to the point of the bypass and a left common carotid artery to left subclavian artery bypass with ligation inferior to the bypass. In another embodiment, for example, an aortic graft assembly of the invention that includes two tubular branch components (e.g., one into the right common carotid, another into the left common carotid) can include a left common carotid artery to left subclavian artery bypass, with ligation of the left subclavian artery inferior to the bypass (see FIGS. 16 and 17). Alternatively, as shown in FIGS. 26A-26C, aortic assembly systems can be implanted in the abdominal aorta 300. Opening 84 can be placed in abdominal aorta proximate to celiac artery 302, superior mesenteric artery 304 or renal artery 306, thereby spanning aneurysm 308. Tubular branch component 254 can then be implanted into at least one of celiac artery 302, superior mesenteric artery 304 or at least one renal artery 306.

In another embodiment, shown in FIGS. 25A and 25B, inner sheath 210 about tubular aortic component 12, includes proximal perforated portion 280 that defines through-holes 282. Through-holes 282 can be defined by a mesh or fabric of perforation portion 280, as shown in FIG. 25A, or as distinct openings, such as longitudinal through-hole opening 284 shown in FIG. 25B. The through-holes permit relatively continuous blood flow during implantation of the prosthesis, as further described in U.S. Published Patent Application No.: 2010/0234932, the teachings of which are incorporated herein by reference in their entirety.

Suitable systems, delivery devices and components of systems, stent grafts as described in U.S. application Ser. No. 11/449,337, filed on Jun. 8, 2006; Ser. No. 11/699,700, filed on Jan. 30, 2007; Ser. No. 11/700,609, filed on Jan. 31, 2007; Ser. No. 11/701,867, filed on Feb. 1, 2007; Ser. No. 11/828,653, filed on Jul. 26, 2007; Ser. No. 12/137,592, filed on Jun. 12, 2008; Ser. No. 11/701,876, filed on Feb. 1, 2007; 61/164,545, filed on Mar. 30, 2009; Ser. No. 12/459,387, filed on Jun. 30, 2009; and U.S. Pat. Nos. 7,763,063; 8,007,605; 8,062,345; 8,062,349; 8,070,790; 8,292,943 and 8,308,790, the teachings of all of which are hereby incorporated by reference in their entirety, can be employed to deliver the aortic graft assembly of the invention by the method of the invention.

The teachings of all patents, published applications and references cited herein are incorporated by reference in their entirety.

Example 1

A 74 year old male with penetrating atherosclerotic ulcer (PAU) of the aorta located on the interior side of the thoracic arch at the level of the left common carotid was treated. A model of the patient's anatomy was made based on computer tomography (CT) scanning. A right carotid to left carotid bypass was performed initially without ligating the left carotid. A tubular aortic component of an aortic graft assembly (46 mm-42 mm×80 mm) was deployed at the sinotubular junction. The ascending aorta of this patent had a graft diameter of about 44 mm. A tubular aortic component having a diameter of 46/42 mm×80 mm was employed to provide a smaller healthy neck. The proximal end of the tubular aortic component of the aortic graft assembly was released to optimize apposition with the wall of the ascending aorta.

A tunnel graft (46 mm-34 mm×220 mm) was used in the aortic graft assembly. The tunnel graft was 15 mm in diameter. The aperture of the tubular aortic component was 30 mm×30 mm. A graft of a size of 15 mm-17 mm×100 mm or 15 mm-17 mm×110 mm) was employed to bridge the graft tunnel with the brachial cephalic trunk and a wire-catheter was positioned prior to implantation as a precautionary bailout. An angiogram was performed to confirm profusion to the and left common carotid arteries. The tunnel graft was advanced to the proximal portion of the aperture of the tubular aortic component with the distal end of at least one tubular branch component. The graft was aligned to allow canulation of the tunnel graft through the innominate or the left common carotid arteries based on movement of the tubular aortic component. The tunnel graft was cannulated via the right common carotid. A relatively short tubular branch component was selected in this patient because the tunnel graft was deployed more distally. The distal end of the branch graft was aligned with the brachial cephalic trunk bifurcation and the tubular branch graft deployed without complication. An angiogram showed exclusion of the aneurysm with flow to the innominate artery and left common carotid artery via a carotid-carotid bypass.

Example 2

An 81 year old male with an aneurysm at the arch of the aorta was treated. A CT scan was employed to model the patient's anatomy. The thoracic aneurysm was in a region of the aortic arch and at least a portion of the descending aorta. The tunnel graft had a diameter of about 15 mm.

While this invention has been particularly shown and described with references to example embodiments thereof, it will be understood by those skilled in the art that various changes in form and details may be made therein without departing from the scope of the invention encompassed by the appended claims.

What is claimed is:

1. A method for implanting a prosthesis, comprising the steps of:
   a) delivering an aortic graft assembly that includes a tubular aortic component through an aorta to an aneurysm site of a patient, the tubular aortic component defining a tunnel lumen and having a proximal end and a distal end connected by a wall, the wall defining a wall aperture that is between the proximal end and the distal end, the wall aperture having a proximal end and a distal end, the proximal end of the wall aperture including an first plane extending perpendicular to a major longitudinal axis of the tubular aortic component when viewed orthogonally to the major longitudinal axis, the tubular aortic component being radially and releasably constrained by a distal clasp at a distal end of an outer control tube of a delivery device, and releasably attached by a retention component to a proximal clasp at the outer control tube proximal to the proximal clasp, the tubular aortic component further supported by a control catheter of the delivery device extending within the outer control tube, the aortic graft assembly further including a tunnel graft extending from the wall aperture and within the tunnel lumen of the tubular aortic component toward the proximal end of the tubular aortic component, wherein the length of the proximal end of the wall aperture in the first plane is greater than the diameter of the tunnel graft lumen in a second plane extending orthogonally to the major longitudinal axis at a point proximal to the proximal end of the wall aperture;
   b) aligning the wall aperture over at least one vessel ostium at the aneurysm site of the patient; and
   c) retracting the outer control tube, thereby releasing the tubular aortic component from the distal and proximal clasps, thereby deploying the tubular aortic component at the aneurysm site in the patient.

2. The method of claim 1, wherein at least one supporting wire extends from the outer control tube, the at least one supporting wire extending through a suture loop inside the proximal end of the tubular aortic component to thereby prevent collapse of the proximal end of the tubular aortic component during deployment.

3. The method of claim 2, further including the step of partially retracting an inner sheath from around the tubular aortic component, whereby the at least one supporting wire at least partially restricts longitudinal movement of the proximal end of the tubular aortic component until the proximal end of the tubular aortic component is secure within the aorta, to thereby prevent collapse of the proximal end of the tubular aortic component at an inferior portion of the aorta.

4. The method of claim 3, wherein the control catheter is curved.

5. The method of claim 4, wherein the wall aperture aligns over two vessel ostiums at the aneurysm site of the patient.

6. The method of claim 2, wherein the at least one supporting wire has at least one stop, the at least one stop limiting movement of the retention component along the at least one supporting wire.

7. The method of claim 3, wherein the inner sheath is releasably secured to a distal end within a cavity defined by a proximal end of a nose cone of the delivery device, and the tubular aortic component further includes a clasping stent at the proximal end of the tubular aortic component, wherein the steps of the method further include:
   a) partially retracting the inner sheath from around the tubular aortic component to release a distal end of the inner sheath from the nose cone and thereby cause partial deployment of the tubular aortic component;
   b) partially retracting the control catheter to thereby release the clasping stent from the distal clasp and the retention component from the proximal clasp;
   c) further retracting the control catheter to at least partially retract the nose cone to within the tubular aortic component while retaining the clasping stent on the supporting wires;
   d) advancing the tubular aortic component to a final position in the aorta of the patient spanning the aneurysm site;
   e) fully retracting the inner sheath from the tubular aortic component; and
   f) fully retracting the nose cone and the supporting wires to release the clasping stent from the supporting wires, thereby fully deploying the tubular aortic component within the aorta of the patient at the aneurysm site.

8. The method of claim 7, wherein the inner sheath defines at least one through hole at a proximal end of the inner sheath.

9. The method of claim 1, further including the step of partially retracting an inner sheath from around the tubular aortic component, and wherein the tubular aortic component and the inner sheath each include a radiopaque marker longitudinally aligned along a path of relative movement of the inner sheath and the tubular aortic component during deployment of the tubular aortic component, and spaced apart from each other, whereby the partial retraction of the inner sheath will cause overlap of the radiopaque marker of the tubular aortic component and the inner sheath.

10. The method of claim 9, wherein the radiopaque markers are on superior portions of the inner sheath and the tubular aortic component.

11. The method of claim 10, wherein the radiopaque marker of the tubular aortic component is elongate and substantially aligned with the major longitudinal axis of the inner sheath.

12. The method of claim 1, wherein the tubular aortic component further includes at least one radiopaque marker.

13. The method of claim 12, wherein the radiopaque marker is located on the tubular aortic component facing away from a concavity of a curve defined by the control catheter.

14. The method of claim 1, further including the step of implanting a tubular branch component through at least one branch artery of the aorta of the patient into the wall aperture and the tunnel graft within the tubular aortic component.

15. The method of claim 1, wherein the retention component is a suture loop.

16. The method of claim 1, wherein the retention component is radiopaque.

17. The method of claim 1, wherein the retention component is at least one of a magnet or stent apex.

* * * * *

UNITED STATES PATENT AND TRADEMARK OFFICE
CERTIFICATE OF CORRECTION

PATENT NO.        : 10,390,930 B2
APPLICATION NO.   : 15/417467
DATED             : August 27, 2019
INVENTOR(S)       : Samuel Arbefeuille et al.

Page 1 of 1

It is certified that error appears in the above-identified patent and that said Letters Patent is hereby corrected as shown below:

In the Claims

In Claim 1 at Column 14, Line 30, after "including an" and before "first plane extending perpendicular to a," insert --arch that lies in a--

Signed and Sealed this
Twenty-second Day of October, 2019

Andrei Iancu
*Director of the United States Patent and Trademark Office*